United States Patent [19]

Claisse et al.

[11] 4,012,377
[45] Mar. 15, 1977

[54] OXADIAZOLE AND OXADIAZOLINE DERIVATIVES

[75] Inventors: John Anthony Claisse, North Harrow; Gordon Ian Gregory, Chalfont St. Peter; William Kingston Warburton, Pinner, all of England

[73] Assignee: Glaxo Laboratories Limited, Greenford, England

[22] Filed: Mar. 7, 1975

[21] Appl. No.: 556,324

Related U.S. Application Data

[63] Continuation-in-part of Ser. No. 473,064, May 24, 1974, abandoned, which is a continuation of Ser. No. 219,873, Jan. 21, 1972, abandoned, which is a continuation-in-part of Ser. No. 59,029, July 28, 1970, abandoned, which is a continuation-in-part of Ser. No. 715,947, March 26, 1968, abandoned.

[52] U.S. Cl. .................. 260/240 D; 260/240 E; 260/240.9; 260/307 G
[51] Int. Cl.² ...................................... C07D 271/06
[58] Field of Search ....... 260/307 G, 240 D, 240 E, 260/240.9

[56] References Cited

UNITED STATES PATENTS

| | | | |
|---|---|---|---|
| 3,192,103 | 6/1965 | Sousa et al. | 260/307 G |
| 3,356,684 | 12/1967 | Buting et al. | 260/307 G X |
| 3,471,621 | 10/1969 | Phillips et al. | 260/307 G X |
| 3,557,099 | 1/1971 | Breuer | 260/307 G |
| 3,574,222 | 4/1971 | Elog et al. | 260/307 G |
| 3,637,707 | 1/1972 | Koch | 260/240.9 UX |

FOREIGN PATENTS OR APPLICATIONS 1,053,825  1/1967  United Kingdom ........... 260/307 G

OTHER PUBLICATIONS

Gyogyszer et al. "Oxadiazolederivatives" in Chem. Abs. vol. 64, 1966 col. 739(a).

*Primary Examiner*—Allen B. Curtis
*Attorney, Agent, or Firm*—Bacon & Thomas

[57] ABSTRACT

There are described new compounds of formula

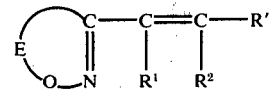

in which E is selected from the group consisting of residues of formula

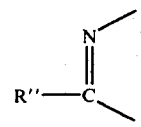

and

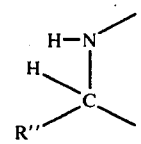

in which R'' is selected from the group consisting of amino, vinyl, allyl, ethynyl, $C_1$–$C_5$ alkyl, $C_1$–$C_5$ alkoxy, or $C_1$–$C_5$ alkylthio or a $C_1$–$C_5$ alkyl group susbstituted by at least one halogen atom; and hydrogen; in which $R^1$ and $R^2$ are each selected from the group consisting of hydrogen, halogen, methyl and ethyl; and R' is selected from substituted phenyl when R'' is other than hydrogen, and phenyl, thienyl and substituted phenyl and thienyl when R'' is hydrogen.

The compounds are useful in the control of parasites. Certain of the compounds have antimicrobial properties.

9 Claims, No Drawings

OXADIAZOLE AND OXADIAZOLINE DERIVATIVES

This application is a continuation-in-part of our application Ser. No. 473,064, filed May 24, 1974, now abandoned, which was in turn a continuation of our application Ser. No. 219,873 filed Jan. 21, 1972, now abandoned, which was in turn a continuation-in-part of our application Ser. No. 59029, filed July 28, 1970 now abandoned, which was in turn a continuation-in-part of our application Ser. No. 715,947, filed Mar. 26th, 1968 and also now abandoned.

BACKGROUND OF THE INVENTION

1. Field of the Invention

This invention relates to the preparation of new oxadiazole derivatives useful in the control of parasites, especially endoparasites.

Parasitic infections of man and animals present a considerable health hazard. Due to their widespread occurrence attempts to find cures for these infections has led to considerable research seeking to find agents which are effective in their control. One parasite of man which is particularly widespread in certain parts of the world is *Entamoeba histolytica*. This parasite generally inhabits the gut and frequently results in death of the host, especially when infestation of the liver occurs in later stages of the infection. In animals such as sheep and cattle, various helminths are also well-known to give rise to a considerable health hazard.

2. Summary of the Invention

We have now found that certain oxadiazole derivatives hereinafter set forth have particularly high action against a variety of parasites.

The invention provides a compound selected from the group consisting of i) a compound of formula

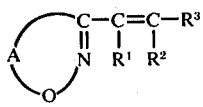

in which A is selected from the group consisting of residues of formula

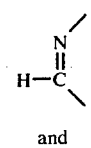

and

$R^1$ and $R^2$ are each selected from the group consisting of a hydrogen atom, a halogen atom and a methyl or ethyl group and where $R^3$ is selected from the group consisting of a phenyl and a thienyl group and such group substituted by at least one substituent selected from the group consisting of halogen, azido, cyano, $C_1$–$C_5$ alkyl, $C_1$–$C_5$ alkoxy, trifluoromethyl, $C_1$–$C_5$ alkylthio, $C_1$–$C_5$ alkylsulfinyl, $C_1$–$C_5$ alkylsulfonyl, thiocyanato, nitro, amino and hydroxy; and ii. a compound of the formula

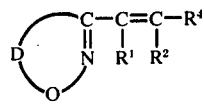

in which D is selected from the group consisting of residues of the formula

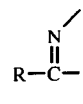

and

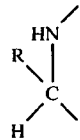

in which R is selected from the group consisting of amino, vinyl, allyl, ethynyl, $C_1$–$C_5$ alkyl, $C_1$–$C_5$ alkoxy, $C_1$–$C_5$ alkylthio or a $C_1$–$C_5$ alkyl group substituted by at least one halogen atom, where $R^1$ and $R^2$ have the above defined meaning, and $R^4$ is a phenyl group substituted by at least one substituent selected from the group consisting of cyano, alkoxy of 1–3 C atoms, hydroxy, mercapto, sulfo, thiocyanato, and a group of formula —$SO_xR^5$ in which x is 0 or the integer 1 or 2 and $R^5$ is ($C_1$–$C_5$) alkyl;

As will appear hereinafter various compounds of formula I are also useful intermediates for the preparation of other compounds of the said formula.

DESCRIPTION OF THE PREFERRED EMBODIMENTS

In the above formulae I and II, $R^1$ and $R^2$ are preferably hydrogen. Examples of other values for $R^1$ and/or $R^2$ are methyl, ethyl, chlorine, bromine, iodine or fluorine.

$R^4$ is preferably a phenyl group substituted by one or more of the above-specified substituents, one of which is in the 4-position.

Examples of particular substituents R in formula II above include, for example, methyl, ethyl, propyl, isopropyl, n-butyl, chloromethyl, trifluoromethyl, trichloromethyl, methoxy and methylthio.

The compounds according to the invention of formula II in particular possess powerfull action against the parasite *Entamoeba histolytica*. In various cases, e.g. those compounds containing a reactive group (such as a hydroxy group or a halogen atom) readily convertible to another group, the compounds are also useful intermediates for the preparation of other such compounds.

The compounds according to the invention of formula I also possess powerful action against parasites including *Nippostrongylus muris, Nematospiroides dubius, Haemonchus contortus, Trichostrongylis colubriformis, Ostertagia circumcincta, Cooperia punctata, Nematodirus battus, Dictyocaulus filaria, Strongyloides papillosus* and *Entamoeba histolytica*.

Compounds according to the invention which are of good anthelmintic activity include particularly:

3-styryl-1,2,4-oxadiazole
3-(p-chlorostyryl)-1,2,4-oxadiazole,
3-(p-cyanostyryl)-1,2,4-oxadiazole,
3-(p-bromostyryl)-1,2,4-oxadiazole,
3-(p-fluorostyryl)-1,2,4-oxadiazole,
4,5-dihydro-3-(p-fluorostyryl)-1,2,4-oxadiazole,
3-(p-azidostyryl)-1,2,4,-oxadiazole,
3-(p-trifluoromethylstyryl)-1,2,4-oxadiazole,
3-β-(5-chlorothien-2-yl)vinyl-1,2,4-oxadiazole,
1-(thien-2-yl)-2-(1,2,4-oxadiazol-3-yl)-ethylene,
3-m-chlorostyryl-1,2,4-oxadiazole,
3-p-methoxystyryl-1,2,4-oxadiazole,
3-(5-methylthiothien-2-yl)vinyl-1,2,4-oxadiazole,
3-p-methylthiostyryl-1,2,4-oxadiazole and
3-p-methylstyryl-1,2,4-oxadiazole.

Compounds according to the invention having particularly good activity against *Entamoeba histolytica* include:

3-p-methylsulfinylstyryl-5-methyl-1,2,4-oxadiazole,
3-p-methylsulfinylstyryl-5-ethyl-1,2,4-oxadiazole,
3-p-methylthiostyryl-5-ethyl-1,2,4-oxadiazole,
3-p-methylthiostyryl-1,2,4-oxadiazole,
3-p-cyanostyryl-1,2,4-oxadiazole,
3-p-thiocyanatostyryl-1,2,4-oxadiazole,
3p-methylsulfonylstyryl-1,2,4-oxadiazole, 5-amino-3-p-methylsulphinylstyryl-1,2,4-oxadiazole and
3-p-methylsulfinylstyryl-1,2,4-oxadiazole,
the last-mentioned compound having particularly high activity.

Certain compounds according to the invention are of interest due to their antimicrobial, e.g. antifungal, antiprotozoal and antibacterial properties, for example, against *Trichophyton mentagrophytes*, *Microsporum canis Candida albicans*, *Trichomonas vaginalis* and *Staphylococus aureus*. Compounds according to the present invention of particular interest by virtue of their antimicrobial properties include, for example.

5-ethyl-3-p-methylthiostyryl-1,2,4-oxadiazole, and 5-chloromethyl-3-p-mthylsulphinylstyryl-1,2,4-oxadiazole.

In some cases as will be clear to those skilled in the art compounds of formulae I and II having various functional groups may be converted into other compounds of formulae I and II by standard chemical transformations, for example as described hereinafter.

Thus, for example, compounds of formula I wherein R represents an aminophenyl group are useful as intermediates for the preparation of corresponding azidophenyl compounds.

The compounds according to the invention have generally low toxicity as determined by toxicity studies in the mouse.

The new compounds according to the invention may be formulated for use in medicine with the aid of suitable carriers or excipients, which may be solid or liquid for example for oral, topical, rectal, intravaginal, or parenteral administration; conventional methods of formulation may be used for this purpose. Convenient forms of composition will vary depending upon the animal to be treated. Suitable compositions include, tablets, capsules, powders, granules, drenches and liquid preparations, e.g. suspensions or emulsions for oral administration, skin paints, lotions, creams, ointments, dusting powders, medicated dressing, eye drops and lotions, and nasal sprays for topical administration, as well as sterile aqueous or oily preparations for injection.

The compositions according to the invention may include other therapeutically effective compounds, for example anti-inflammatory agents such as steroids, e.g. betamethasone-21-phosphate, or antibiotics such as tetracycline.

In the treatment of helminth infections the anthelmintic compounds according to the invention may generally be administered at a dose of from 2 – 200 mg/kg, and preferably 15–20 mg/kg dependent upon the species treated and the nature of the parasite.

In the treatment of amoebic and microbial infections, a daily dose of from 0.5 – 100 mg/kg, preferably 1 – 60 mg/kg, is generally convenient. A relatively low dose of, for example 1 – 20 mg/kg will frequently be sufficient.

When dosage units are used in the treatment of amoebic infections, such units conveniently contain from 2 mg to 500 mg of active ingredient, preferably 2 to 250 mg.

As will be clear to those skilled in the art, dependent upon the infection a single administration may sometimes suffice, but, as with other antiparasitic drugs, one or more additional administrations may be necessary effectively to control the parasitic infection.

For many purposes dosage unit preparations are convenient in medicine, especially tablets and capsules. Each such dosage unit conveniently contains from 0.1 mg. to 5000 mg. of active ingredient, preferably 100 to 2500 mg. dependent on the species for which the preparation is intended. For veterinary purposes, unitary preparations e.g. in sealed packet form adapted for example for the preparation of drenches, may be convenient, each unit containing for example 5 – 50 g. of active ingredient.

The new compounds of formula I or II according to the invention may be prepared generally by reacting an amidoxime of formula

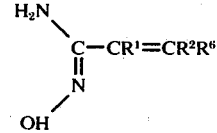

V (wherein R⁶ represents, a group R³ or R⁴ as defined above) with an acylating reagent derived from formic acid or an acid RCOOH or with formaldehyde, an aldehyde RCHO or a compound yielding such an aldehyde.

The reaction with an acylating reagent, generally yields directly a compound of formula I or II containing a double nitrogen-carbon bond in the 4,5-position, whereas when an aldehyde (or a compound yielding an aldehyde) is used, the resulting product is a 4,5-dihydro compound. However, in some cases an O-acyl derivative of the compound of formula V is produced as an intermediate which may not spontaneously cyclise. In such cases, the intermediate O-acyl compound may be cyclised for example, by heating, conveniently in a solvent such as benzene or toluene, under reflux.

The reaction of compounds of formula V with an acylating agent is based generally upon the classical Tiemann acylation synthesis and may be carried out by methods generally used in such acylations.

Thus for example suitable formylating reagents which are required for the preparation of compounds according to the invention of formula I include alkyl orthoformates, e.g. triethyl orthoformate, tripropyl orthoformate etc., alkyl formates, e.g. ethyl formate, formic acid, formamide, the Wilsmeier-Haack reagent (the name given to the complex formed between dimethyl formamide and phosphorus oxychloride), mixed anhydrides with formic acid, e.g., the mixed anhydride of acetic and formic acids, formyl halides e.g. formyl fluoride. The reaction with the formylating reagent may in some cases be carried out with advantage in the presence of an acid catalyst, e.g. a mineral acid such as sulphuric acid, or a Lewis acid e.g. boron trifluoride, stannic chloride or aluminium chloride; the acid catalyst serves to increase the rate of reaction and/or reduce the formation of by-products. The reaction may be carried out in the presence of an inert solvent, e.g. toluene, xylene or dioxan although in many cases, e.g. with the alkyl orthoformates, the formylating agent may serve as the solvent. The reaction is generally effected at temperatures between 60° and 200° C, although formyl halides are preferably used at lower temperatures, e.g. of the order of −78° C.

The reaction of compounds of formula V with formaldehyde is preferably carried out in the presence of a solvent e.g. water, or lower alcohol, dioxan etc., preferably at temperatures between 50° and 150° C. In place of formaldehyde a formaldehyde yielding substance can be used such as a polymer of formaldehyde e.g. paraformaldehyde, etc.

Suitable acylating reagents required for the preparation of compounds of formula II include the appropriate alkyl orthoacylates, e.g. triethyl orthoacetate, tripropyl orthoacetate etc., alkyl or alkenyl esters of carboxylic acids, e.g. ethyl acetate, carboxylic acids, carboxylic acid anhydrides or mixed anhydrides, or carboxylic acid halides, e.g. acetyl chloride or propionyl or trichloroacetyl chloride.

When the acylating agent is an alkyl orthoacylate or an alkyl or alkenyl ester of a carboxylic acid, the acylation is preferably effected in the presence of an acid catalyst e.g. a mineral acid such as sulphuric acid, or a Lewis acid, e.g. boron trifluoride, stannic chloride or aluminium chloride. Where the acylating agent is a carboxylic acid halide the acylation is preferably effected in the presence of an acid binding agent, preferably a tertiary organic base, e.g. pyridine, dimethylaniline or trimethylamine. In the case of acylation using an acid anhydride generally no catalyst is required although in some cases the presence of a base, e.g. a tertiary amine may be advantageous.

The acylation reaction may be carried out in the presence of an inert solvent e.g. toluene, xylene or dioxan although in many cases, e.g. with the alkyl orthoesters the acylating agent may serve as the solvent. The reaction is generally effected at temperatures between 60° and 200° C, although acyl halides are preferably used at lower temperatures.

The preparation of the new compounds wherein R represents an amino, $C_1$–$C_5$ alkoxy or $C_1$–$C_5$ alkylthio group may conveniently be effected by replacing another group R suitable for the purpose, e.g. a trichloromethyl group or a halogen atom, advantageously a chlorine atom. The reaction may, for example, be effected in a solvent, such as an ether e.g. diethyl ether or dioxan or another inert organic solvent such as a hydrocarbon or a chlorinated hydrocarbon, or an alcohol, e.g. methanol.

The preparation of compounds of formula II wherein R represents a primary amino group may conveniently be effected by reacting a corresponding compound wherein R represents a halogen atom or a trichloromethyl group, with ammonia for example, in the form of liquid ammonia.

Compounds wherein R represents an $C_1$–$C_5$ alkoxy or $C_1$–$C_5$ alkylthio group may, for example, be prepared by reacting a corresponding compound wherein R represents a halogen atom or a trichloromethyl group with an alcohol or a thio or an alkali metal e.g. sodium or potassium derivative thereof. When the compound produced is a compound wherein R represents an alkoxy group, the reaction may conveniently be effected in solution in the alcohol concerned or the alcohol from which the alkali metal derivative has been prepared. If a compound wherein R represents a methoxy group is prepared the solvent is preferably methanol. An acid binding agent is generally required when an alcohol or a thiol is reacted with the halo or trichloromethyl compound and this may, for example, be a tertiary organic base, such as triethylamine or pyridine or an inorganic base such as an alkali metal hydroxide, an alkali metal carbonate or an alkali metal bicarbonate.

The preparation of the new compounds wherein R represents an amino, $C_1$–$C_5$ alkoxy or alkylthio group is advantageously effected in the presence of an acid binding agent. The acid binding agent may be a tertiary organic base, e.g. triethylamine or pyridine or an inorganic base such as an alkali metal hydroxide, or an alkali metal carbonate or an alkali metal bicarbonate. In those cases wherein R represents an amino group an excess of ammonia may be used as the acid binding agent.

The reaction of compounds of formula V with an aldehyde (e.g. acetaldehyde) is preferably carried out in the presence of a solvent e.g. water, or lower alcohol, dioxan etc., preferably at temperatures between 50 and 150° C. In place of an aldehyde an aldehyde-yielding substance e.g. an acetal can be used.

4,5-Dihydro compounds of formulae I and II may be converted into the corresponding 4,5-unsaturated compounds by oxidation for example using manganese dioxide, potassium or sodium permanganate, sodium nitrite, ferric chloride, palladised charcoal and air, chloranil or related quinones etc. This reaction is conveniently effected in a solvent the nature of which will depend upon the oxidising agent used. Suitable solvents include for example methanol, chloroform and ethyl acetate.

The temperature at which the oxidation is carried out will also depend on the oxidising agent used but will generally be between 0° and 100° C.

It will be appreciated that for compounds of formula I or II bearing certain substituents in the groups $R^3$ and $R^4$ it may be preferable first to prepare a compound of formula I or II having a different substituent by a method as set forth above, which substituent is thereafter converted to the desired substituent. Thus for example, if it is desired that $R^3$ or $R^4$ be an aminophenyl, halophenyl, azidophenyl, thiocyantophenyl or a cyanophenyl group, it is convenient first to prepare a compound in which $R^3$ or $R^4$ is nitrophenyl, the nitro group being then reduced to an amino group, which latter may then, if desired, be converted to, for example, a cyano, thiocyanato or azido group or halogen atom e.g. by a Sandmeyer reaction. Furthermore compounds bearing alkylsulphinyl and alkyl sulphonyl groups in the groups $R^3$ and $R^4$ may advantageously be prepared from the corresponding alkylthio compounds by oxidation, for example, by the use of a peracid such as peracetic acid; where it is desired to form an alkyl-sulphinyl group, in general approximately one equivalent of oxidising agent will be used.

It should be noted that the carrying out of transformations upon substituents in the groups $R^3$ or $R^4$ e.g. oxidation, in compounds of the oxadiazolinyl series may result in oxidation of the oxadiazoline ring to an oxadiazole ring.

As will be appreciated the compounds of formulae I and II, exist in cis- and trans-forms both of which are comprehended within the invention. Generally the amidoxime used as starting material will have the trans-configuration and hence the resulting oxadiazole will usually be recovered as the trans-form, from which the cis-form may be obtained by photoisomerisation for example on solution in ethanol. In general, the trans-forms are preferred.

EXAMPLE 1

3-($\beta$-trans-Styryl)-1,2,4-oxadiazole

Cinnamamidoxime (6.5 g.) (H. Wolff, Ber., 1886, 19, 1507) was refluxed in triethylorthoformate (60 ml.) containing two drops of boron trifluoride etherate. Thin layer chromatography showed that receiving was complete after 1 hr. and the reaction mixture was evaporated in dryness in vacuo. The residue was dissolved in chloroform (100 ml.) and washed consecutively with 2N-hydrochloric acid (100 ml.), saturated sodium bicarbonate solution (100 ml.) and water (100 ml.). The chloroform solution was evaporated to dryness in vacuo and the resultant yellow crystals were recrystallised from aqueous methanol to yield needle-like crystals of 3-($\beta$-trans-styryl)-1,2,4-oxadiazole 5.82 g. (84%), m.p. 82°, $\lambda$max (EtOH) 275 nm., $\epsilon$23200, $\tau$(CDCl$_3$) 1.33 (1H), 2.56 (aromatic multiplet), 2.24 (doublet, J=16 c./sec.), 2.88 (doublet, J=16 c./sec.) (Found: C, 69.9; H, 4.7; N, 15.9. $C_{10}H_8N_2O$ requires C, 69.75; H, 4.7; N, 16.3%).

EXAMPLE 2 a. p-Chlorocinnamamidoxime

Hydroxylamine hydrochloride (13.0 g.) was dissolved in dry methanol (100 ml.) and neutralised to phenolphthalein with a solution of sodium (6 g.) in methanol (60 ml.). The precipitated sodium chloride was filtered off and the filtrate was refluxed with p-chlorocinnamonitrile (9.4 g.) for 2 hrs. Thin layer chromatography showed the reaction to be complete after this time. The reaction mixture was evaporated to dryness in vacuo and the residue was crystallised from ethanol to produce colourless of crystals of p-chlorocinnamamidoxime, 4.16 g. (37%) m.p. 102°–4° $\lambda_{max}$(EtOH), 273 nm., $\epsilon$17500, $\tau$(CDCl$_3$) 2.68 (aromatic), 3.00 (OH), 5.16 (NH$_2$), 3.13 (doublet, J=16 c./sec.), 3.58 (doublet, J=16 c./sec.). p-Chlorocinnamonitrile was prepared by NH$_2$OH treatment and dehydrations of p-chlorocinnamaldehyde (J. Chem. Soc., 1965, 1564). p-Chlorocinnamaldehyde was prepared from p-chloro benzaldehyde and CH$_3$CHO cf. G. Cigarella, E. Occelli, and E. Testa, (J. Med. Chem., 1965, 8, 326).

3-($\beta$-trans-p-chlorostyryl)-1,2,4-oxadiazole p-Chlorocinnamamidoxime (4.0 g.) was refluxed in triethylorthoformate (40 ml.) containing two drops of boron trifluoride etherate for 15 min. Thin layer chromatography after 5 mins. showed the reaction to be complete. The reaction mixture was evaporated in vacuo to a yellow solid which was dissolved in chloroform (100 ml.) and washed consecutively with 2N-hydrochloric acid (100 ml.), saturated sodium bicarbonate solution (100 ml.) and water (100 ml.). The chloroform solution was evaporated to dryness in vacuo and the yellow crystalline residue was recrystallised frm methanol to yield yellow crystalline platelets of 3-($\beta$-trans-p-chlorostyryl)-1,2,4-oxadiazole, 3.33 g. (79%), m.p. 134°, $\lambda$max. (EtOH) 220–221, 280 nm., $\epsilon$ 14600, 30500, $\tau$(CDCl$_3$) 1,32 (1H), 2.58 (aromatic singlet), 2.30 (doublet, J=16 c./sec.), 2.92 (doublet, J=16 c./sec.) (Found: C, 57.9; H, 3.8; N, 13.3; Cl, 17.3. $C_{10}H_7ClN_2O$ requires C, 58.1; H, 3.4; N, 13.6; Cl, 17.2%).

EXAMPLE 3 a. $\beta$-Methyl-p-chlorocinnamonitrile p-Chloroacetophenone (31 g.), cyanoacetic acid (25 g.), ammonium acetate (5 g.), glacial acetic acid (5 ml.), and benzene (60 ml.) were refluxed together with water separation for 90 hrs., after which time approximately 9 ml. of water had been collected. Removal of benzene and distillation of the residue gave a fraction, b.p. 115°–125°/1 mm., which was dissolved in chloroform (100 ml.) and washed with saturated sodium hydrogen carbonate solution (50 ml.) and water (50 ml.), and dried over sodium sulphate. The extract was evaporated to a viscous oil under reduced pressure and the residual oil was distilled under high vacuum to give $\beta$-methyl-p-chlorocinnamonitrile 17.5 g. (49%), b.p. 106°–113°/0.5 mm., $\lambda_{max}$. (EtOH) 271 nm ($\epsilon$ 19350) (Found: C, 57.8; H, 4.7; Cl, 19.7; N, 8.1. $C_{10}H_8ClN$ requires C, 67.6; H, 4.5; Cl, 20.0; N, 7.9%).

b. $\beta$-Methyl-p-chlorocinnamamidoxime $\beta$-Methyl-p-chlorocinnamonitrile (17.0 g.) in dry methanol (100 ml.) was treated with the methanolic hydroxylamine solution (120 ml.) prepared by neutralising a methanolic solution of hydroxylamine hydrochloride (14.0 g.) with sodium methoxide, and the mixture was refluxed for ca. 12 hr. The reaction mixture was evaporated to an oil under reduced pressure, the residue was dissolved in chloroform (200 ml.) and extracted into 2N hydrochloric acid (500 ml.). The acid solution was then neutralised with sodium hydrogen carbonate solution and the insoluble material was extracted into chloroform (200 ml.). The extract was dried over sodium sulphate and evaporated to a pale-green crystalline solid in vacuo, giving crude $\beta$-methyl-p-chlorocinnamamidoxime 8.6 g. (43%). Further extraction of the aqueous solution with more chloroform (200 ml.) produced a second crop of product 4.64 g. (23%). Recrystallisation from aqueous methanol gave pale-green crystals of $\beta$-methyl-p-chlorocinnamidoxime, m.p. 134°–136°, $\lambda_{max}$. (EtOH) 254 nm ($\epsilon$ 14240) (Found: C, 57.0; H, 5.3; Cl, 16.7; N, 13.1. $C_{10}H_{11}ClN_2O$ requires C, 57.0; H, 5.2; Cl,, 16.8; N, 13.3%).

c. 3-($\beta$-Methyl-p-chlorostyryl)-1,2,4-oxadiazole $\beta$-Methyl-p-chlorocinnamamidoxime (4.64 g.) was refluxed with ethyl orthoformate (50 ml.) and two drops of boron trifluoride etherate for 45 min. Ethyl orthoformate was removed under reduced pressure and the residual brown oil was dissolved in chloroform (100 ml.) and washed consecutively with 2N-hydrochloric acid (20 ml.), saturated sodium hydrogen carbonate solution (20 ml.), and water (20 ml.). The chloroform solution was evaporated to a brown oil (ca. 4.6 g.) which was chromatographed on silica gel. Elution with benzene gave 3-(β-methyl-p-chlorostyryl)-1,2,4-oxadiazole, 2.90 g. (60%), m.p. 56°–57°, $\lambda_{max}$ (EtOH) 273 nm ($\epsilon$ 20760) (Found: C 59.95; H, 4.2; Cl, 15.9; N, 12.7. $C_{11}H_9ClN_2O$ requires C, 59.85; H, 4.1; Cl, 16.1; N, 12.7%).

EXAMPLE 4 a. β-(Thien-2-yl) acrylamide

Methyl-β-(thien-2-yl) acrylate (22.7 g.) was dissolved in dry ethanol (50 ml.) and divided equally between four Carius tubes. Ammonia solution (0.880, 100 ml.) was added to each tube, which was sealed and heated at 115°–120° for 22 hr. Removal of solvent under reduced pressure and recrystallisation from aqueous methanol gave β-(thien-2-yl) acrylamide, 4.43 g. (21%) m.p. 153°, $\lambda_{max}$ (EtOH) 304–306 nm., ($\epsilon$ 18850) (Found: C, 54.4; H, 4.6; N, 9.3; S, 20.4. $C_7H_7NOS$ requires C, 54.9; H, 4.6; N, 9.15; S, 20.9%).

b. β-(Thien-2-yl) acrylonitrile

β-(Thien-2-yl) acrylamide (5.2 g.) was mixed with sodium metabisulphite (12.9 g.) and heated with phosphoryl chloride (2.4 ml.) on a steam bath. After 1 hr., more phosphoryl chloride (10 ml.) was added and the mixture heated for a further 3.5 hrs. The mixture was cooled in an ice-bath and iced water cautiously added. The mixture was extracted into chloroform and the chloroform layer was washed with saturated sodium hydrogen carbonate solution, dried over sodium sulphate, and evaporated in vacuo to a brown oil. Distillation gave β-(thien-2-yl) acrylonitrile, 1.50 g. (33%), b.p. 82–86°/0.5 mm., $\lambda_{max}$ (EtOH) 306 nm, ($\epsilon$ 18600).

c. β-(Thien-2-yl) acrylamidoxime

β-(Thien-2-yl) acrylonitrile (2.78 g.) was dissolved in dry methanol (60 ml.) and treated with a solution of hydroxylamine in methanol (60 ml.) (prepared by dissolving hydroxylamine hydrochloride (6 g.), in methanol (60 ml.) and neutralising with sodium methoxide in methanol). The solution was refluxed for 6 hr. and left overnight to cool. Evaporation in vacuo left a brown oil which was dissolved in chloroform and washed with water (10 ml.). The chloroform solution was evaporated to dryness leaving the crude amidoxime, 2.76 g. (80%). Recrystallisation from aqueous methanol gave β-(thien-2-yl) acrylamidoxime, m.p. 92°, $\lambda_{max}$ (EtOH) 306 nm, ($\epsilon$ 20070) (Found: C, 49.7; H, 4.7; N, 16.8; S, 18.7. $C_7H_8N_2OS$ requires C, 50.0; H, 4.8; N, 16.7; S, 19.05%).

d. trans-1-(Thien-2-yl)-2-(1,2,4-oxadiazol-3-yl)-ethylene

β-(Thien-2-yl) acrylamidoxime (2.20 g.) was refluxed in ethyl orthoformate (30 ml.) containing one drop of boron trifluoride etherate. After 1 hr. the ethyl orthoformate was removed under reduced pressure and the residue was dissolved in chloroform (20 ml.) and washed consecutively with 2N hydrochloric acid (20 ml.), saturated sodium hydrogen carbonate solution (20 ml.), and water (20 ml.). Evaporation of the chloroform solution to dryness and chromatography in benzene on silica gel gave trans-1-(thien-2-yl)-2-(1,2,4-oxadiazol-3-yl)-ethylene 1.57 g. (67%), m.p. 78°, $\lambda_{max}$ (EtOH) 306 nm, ($\epsilon$ 21700) (Found: C, 52.9; H, 3.7; N, 15.3; S, 17.2. $C_8H_6N_2OS$ requires C, 53.9; H, 3.4; N, 15.7; S, 18.0%).

EXAMPLE 5 a. p-Nitrocinnamamidoxime p-Nitrocinnamonitrile (8.12 g.) was added at 30° 35° to an anhydrous methanolic hydroxylamine solution (320 ml.) prepared by neutralising hydroxylamine hydrochloride (13.00 g.) with methanolic sodium methoxide. The solution was refluxed for 2.5 hr. and left overnight. Removal of the solvent and washing with water left the crude amidoxime, 7.07 g. (74%), m.p. 184–185° (decomp.). Recrystallisation of a sample from ethanol gave p-nitrocinnamamidoxime as yellow needles, m.p. 184°–186°, $\lambda_{max}$ (EtOH) 235.5, 265, 344 nm, ($\epsilon$ 10020, 10000, 14800) (Found: C, 51.7; H, 4.7; N, 20.0. $C_9H_9N_3O_3$ requires C, 52.2; H, 4.4; N, 20.3%).

b. 3-trans-p-Nitrostyryl-1,2,4-oxadiazole p-Nitrocinnamamidoxime (1.00 g.) was suspended in ethyl orthoformate (5 ml.). Boron trifluoride etherate (1 drop) was added, and the mixture slowly heated to the boiling point in an oil-bath. The amidoxime dissolved, then after ca. 2 min. yellow needles appeared. The mixture was refluxed for 5 min. more, cooled, and the ethyl orthoformate was removed under reduced pressure. The residual solid was washed with light petroleum (b.p. 40°–60°), leaving the crude oxadiazole, (0.98 g.) (93%). m.p. 211°–214°. Recrystallisation from methanol gave 3-trans-p-nitrostyryl-1,2,4-oxadiazole, yellow needles, m.p. 225°–226°, $\lambda_{max}$ (EtOH) 308 nm, ($\epsilon$ 21000) (Found: C, 55.3; H, 3.5; N, 19.4. $C_{10}H_7N_3O_3$ requires C, 55.3; H, 3.25; N, 19.35%).

EXAMPLE 6

3-trans-p-Aminostyryl-1,2,4-oxadiazole 3-p-Nitrostyryl-1,2,4-oxadiazole (2.17 g.) in acetone (220 ml.) was reduced with acid chromous chloride solution. (N, 75 ml.). The acetone was removed after ca. 5 min., then some water (ca. 35 ml.) was removed under reduced pressure and the suspension refrigerated overnight. Filtration gave grey crystals of the amine hydrochloride, which were pressed as dry as possible on the filter, then dissolved in water (60 ml.). A red impurity was filtered off, and the filtrate neutralised to pH 6–7 (solid sodium hydrogen carbonate). The suspension was extracted several times with chloroform (total vol. 75 ml.), and the chloroform washed with water and dried (MgSO₄). Evaporation of the chloroform left 3-trans-p-aminostyryl-1,2,4-oxadiazole as small, pale-yellow needles, 1.40 g. (75%), m.p. 139.5°–140.5°, $\lambda_{max}$ (CHBr₃) 3390, 3485 (NH₂), 975 (CH = CH, trans), 820 cm.$^{-1}$ (aromatic), $\tau$(CDCl₃) 6.13 (NH₂); 3.38, 2.65 (aromatic); 2.38, 3.15 (CH = CH); 1.44 (CH). The picrate had m.p. 175° (decomp.) (from ethanol) (Found: C, 46.3; H, 3.1; N, 19.9. $C_{16}H_{12}N_6O_8$ requires C, 46.2; H, 2.9; 20.2%).

EXAMPLE 7

3-cis-p-Chlorostyryl)-1,2,4-oxadiazole 3-(β-trans-p-chlorostyryl)-1,2,4-oxadiazole (3.0 g.) was dissolved in absolute alcohol (1500 ml.) and irradiated at room temperature for 23 hr. under nitrogen using a medium pressure mercury vapour arc tube contained in a water cooled glass well immersed in the solution. Ultraviolet spectra of suitably diluted aliquots showed a change from $\lambda_{max}$ 280 nm ($E_{1cm}^{1\%}$ 1540) to $\lambda_{max}$ 277 nm ($E_{1cm}^{1\%}$ 1140). The irradiated solution was then concentrated to a small volume (ca. 80 ml.) and left at 0° for 1 hr. when white crystals (0.83 g.), m.p. 133° of the trans isomer were recovered. Concentration of the mother liquors to ca. 20 ml. gave a second crop of the starting material (0.14 g.). The mother liquors were evaporated to dryness to give the crude cis-isomer (2.2 g., solvated) as a pale yellow solid, m.p. 36°.

The irradiation experiment was repeated to give another sample of the crude cis-isomer (2.2 g.), m.p. 38°. The products were combined, dissolved in petroleum spirit (200 ml., b.p. 40°–60°), the colourless solution was decanted from a small amount of a yellow gum and concentrated to incipient crystallisation. Cooling to 0° gave the title compound (2.9 g.), m.p. 46°, $\lambda_{max}$. (EtOH) 276 nm ($\epsilon$ 17,300); no trace of the trans isomer was apparent in the infrared or proton magnetic resonance spectra. (cis protons, $\tau$(CDCl$_3$) 3.98 and 4.49 (J = 13)). A second crop (0.5 g.), m.p. 45°, $\lambda_{max}$. (EtOH) 275 nm ($\epsilon$ 16000) was obtained from the mother liquors on concentration. The recrystallised sample had the following analysis (Found: C, 58.4; H, 3.45; Cl, 17.1; N, 13.6. $C_{10}H_7ClN_2O$ requires C, 58.1; H, 3.4; Cl, 17.2; N, 13.6%).

EXAMPLE 8

3-(cis-Styryl)-1,2,4-oxadiazole 3-(trans-Styryl)-1,2,4-oxadiazole (0.75 g.) in absolute ethanol (750 ml.) was irradiated at room temperature, under nitrogen for a total of 31 hr. using a medium pressure mercury vapour arc tube contained in a water cooled glass well immersed in the solution. The ultraviolet spectra of suitably diluted aliquots showed a reduction in the intensity of absorption at ca. 274 nm over the period of irradiation. The colourless solution was evaporated to a low volume when the trans isomer (0.11 g.), m.p. 84°, $\lambda_{max}$. (EtOH) 274 nm ($\epsilon$ 26,200) separated. Evaporation of the mother liquors to dryness gave a solid and an oil. The oil was separated and thoroughly dried to give 3-(cis-styryl)-1,2,4-oxadiazole contaminated with ca. 25% by weight of the trans-isomer, $\lambda_{max}$. (EtOH) 272–273 nm ($\epsilon$ 14,300), pmr. shows cis-protons at 2.92 and 3.50 (J = 12.5) and confirms the presence of the transisomer.

EXAMPLE 9

3-trans-p-Chlorostyryl-4,5-dihydro-1,2,4-oxadiazole p-chlorocinnamamidoxime (4.00 g.) was partly dissolved in boiling water (320 ml.), and 37% aqueous formaldehyde (12 ml.) was added. The mixture was refluxed for 30 min. and allowed to cool overnight. The solid that separated was washed with water, leaving the crude oxadiazoline, 3.68 g. (87%), m.p. 168° (decomp.). Recrystallisation (3.5 g.) from ethanol (50 ml.) gave 3-(trans-p-chlorostyryl)-4,5-dihydro-1,2,4-oxadiazole 3.18 g. (75%), m.p. 176°–178° (decomp.), $\lambda_{max}$. (EtOH) 274 nm ($\epsilon$ 22000), $\tau$(Me$_2$SO) 4.69 (CH$_2$); 2.97 (NH), 3.17, 2.81 (doublet, J = 17; CH = CH); 2.32, 2.55 (aromatic) (Found: C, 57.55; H, 4.4; N, 13.0; Cl, 16.7. $C_{10}H_9ClN_2O$ requires C, 57.6; H, 4.3; N, 13.4; Cl, 17.0).

EXAMPLE 10

Dehydrogenation of 3-(trans-p-chlorostyryl)-4,5-dihydro-1,2,4-oxadiazole 3-(trans-p-Chlorostyryl)-4,5-dihydro-1,2,4-oxadiazole (50 mg.) in chloroform (5 ml.) was stirred with active manganese dioxide (500 mg.) for 2 hr. Dehydrogenation was incomplete as judged by thin layer chromatography. More manganese dioxide (1.5 g.) was added with chloroform (5 ml.) and stirring was continued for 24 hr. Filtration and evaporation of the filtrate left 3-(trans-p-chlorostyryl)-1,2,4-oxadiazole (50 mg.), m.p. 127°–34°, identified by comparison of its infrared spectrum and mobility on thin layer chromatography with that of an authentic sample (m.p. 133°–134° C).

Small scale experiments showed the above oxadiazole to be similarly dehydrogenated at room temperature with the following reagents:

potassium permanganate in acetic acid/2N–H$_2$SO$_4$,
ferric chloride in ethanol,
palladium charcoal/ethanol in the presence of air,
and sodium nitrite in acetic acid/2N–H$_2$SO$_4$.

The following Examples 11–18 were conducted similarly to Example 2b; in each case refluxing was continued until thin-layer chromatography showed that the reaction was complete.

EXAMPLE 11

3-trans-m-Chlorostyryl-1,2,4-oxadiazole

Yield 66%, m.p. 102–103°, $\lambda_{max}$. (EtOH) 223–224, 273 nm, $\epsilon$ 18040, 24300 (Found: C, 58.05; H, 3.8; N, 13.5; Cl, 17.3. $C_{10}H_7ClN_2O$ requires C, 58.1; H, 3.4; N, 13.6; Cl, 17.2%).

EXAMPLE 12

3-trans-o-Chlorostyryl-1,2,4-oxadiazole

Yield 43%, m.p. 59–61°, $\lambda_{max}$. (EtOH) 224, 275 nm, $\epsilon$ 15900, 25300 (Found: C, 58.2; H, 3.4; N, 13.6; Cl, 17.4. $C_{10}H_7ClN_2O$ requires C, 58.1; H, 3.4; N, 13.6; Cl, 17.2%).

EXAMPLE 13

3-trans-p-Fluorostyryl-1,2,4-oxadiazole

Yield 79%, m.p. 97–99°, $\lambda_{max}$. (EtOH) 272 nm, $\epsilon$ 23760 (Found: C, 63.5; H, 3.8; N, 14.95; F, 9.6. $C_{10}H_7FN_2O$ requires C, 63.15; H, 3.7; N, 14.75; F, 10.0%).

EXAMPLE 14

3-trans-p-Methylstyryl-1,2,4-oxadiazole

Yield 59%, m.p. 95–96°, $\lambda_{max}$. (EtOH) 284 nm, $\epsilon$ 28400 (Found: C, 70.0; H, 5.4; N, 14.9. $C_{11}H_{10}N_2O$ requires C, 71.0; H, 5.4; N, 15.0%).

EXAMPLE 15

3-trans-p-Methoxystyryl-1,2,4-oxadiazole

Yield 78%, m.p. 85°–86°, $\lambda_{max}$. (EtOH) 225, 294 nm, $\epsilon$ 13200, 24400 (Found: C, 65.0; H, 5.05; N, 13.6. $C_{11}H_{10}N_2O_2$ requires C, 65.3; H, 5.0; N, 13.9%).

EXAMPLE 16

3-p-Chloro-α-methylstyryl-1,2,4-oxadiazole

Yield 67%, m.p. 61°–62°, $\lambda_{max}$. (EtOH) 272 nm, $\epsilon$ 26000 (Found: C, 59.8; H, 4.2; N, 12.1; Cl, 16.0. $C_{11}H_9ClN_2O$ requires C, 59.85; H, 4.1; N, 12.7; Cl, 16.05%).

EXAMPLE 17

3-trans-p-Methylthiostyryl-1,2,4-oxadiazole

Yield 39%, m.p. 116°, $\lambda_{max}$. (EtOH) 236–237, 322 nm, $\epsilon$ 11200, 24800 (Found: C, 60.5; H, 4.8; N, 12.5. $C_{11}H_{10}N_2OS$ requires C, 60.5; H, 4.6; N, 12.8%).

EXAMPLE 18

3-trans-p-Trifluoromethylstyryl-1,2,4-oxadiazole

Yield 67%, m.p. 122°–123° (aqueous methanol), $\lambda_{max}$ (EtOH) 273 nm, $\epsilon$ 30000 (Found: C, 54.9; H, 3.1;

F, 24.25; N, 11.8. $C_{11}H_7F_3N_2O$ requires C, 55.0; H, 2.9; F, 23.75; N, 11.7%).

EXAMPLE 19

3-trans-p-Nitrostyryl-1,2,4-oxadiazole 3-trans-Styryl-1,2,4-oxadiazole (1.0 g.) in acetic anhydride (3.5 ml.) was added during 20 min. at −20 to −30° to a stirred mixture of acetic anhydride (4 ml.) and fuming nitric acid (d 1.5; 2 ml.), and the mixture was stirred for a further 20 min. at −20°. The solid that separated was filtrated off and washed with a little cold acetic anhydride, then dissolved in chloroform. The chloroform layer was washed with water and dried and evaporated leaving 100 mg. of a solid, which was shown by infrared spectra, thin-layer, and gas-liquid chromatography to be 3-p-nitrostyryl-1,2,4-oxadiazole, recrystallisation from ethanol gave the nitro derivative m.p. and mixed m.p. 225°–226°. The filtrate was poured into ice and water, giving a solid which was purified by washing a solution in chloroform with water, and evaporating. The residue (550 mg.) was shown by infrared spectra and gas-liquid chromatography to be crude 3-p-nitrostyryl-1,2,4-oxadiazole.

EXAMPLE 20

3-trans-p-Aminostyryl-1,2,4-oxadiazole 3-trans-p-Nitrostyryl-1,2,4-oxadiazole (9.40 g.) was dissolved in warm acetone (865 ml.). The solution was stirred, and acid titanous chloride solution (320 ml., 15% w/v) was added during 20 min. After 20 min. more, the acetone and some water (ca. 40 ml.) were removed under reduced pressure. A second batch of the nitro-compound (9.40 g.) was similarly reduced. After refrigeration, the hydrochlorides that separated were filtered off and combined. The hydrochloride was washed with ice-cold N hydrochloric acid (30 ml.), sucked as dry as possible, and dissolved in water (700 ml.). The pH of the solution was adjusted to 7 (solid sodium hydrogen carbonate), and the resulting suspension extracted with chloroform (1 l.). The chloroform solution was filtered, washed with water, and dried ($CaSO_4$). Evaporation to dryness left crude 3-trans-p-aminostyryl-1,2,4-oxadiazole (14.10 g., 87%), m.p. 140°–141.5°. This material was suitable for further use. A sample recrystallised from benzene-petroleum ether (b.p. 100°–120°) had m.p. 141°, $\lambda_{max}$. (EtOH) 232, 336 nm, ε 10000, 24000 (Found: C, 64.2; H, 5.1; N, 22.5. $C_{10}H_9N_3O$ requires C, 64.2; H, 4.85; N, 22.45%).

The following Examples 21–23 were carried out following the procedure of Example 9.

EXAMPLE 21

3-trans-Styryl-4,5-dihydro-1,2,4-oxadiazole

57% yield, m.p. 121°–122° (from aqueous ethanol). $\lambda_{max}$. (EtOH) 272 nm. ε 17550 (Found: C, 68.4; H, 5.4; N, 16.0. $C_{10}H_{10}N_2O$ requires C, 68.9; H, 5.4; N, 16.1%).

EXAMPLE 22

3-trans-p-Fluorostyryl-4,5-dihydro-1,2,4-oxadiazole

84% yield, m.p. 137°–139° (from aqueous ethanol), $\lambda_{max}$. (EtOH) 270 nm, ε 19630 (Found: C, 62.7; H, 4.5; F, 9.8; N, 15.0. $C_{10}H_9FN_2O$ requires C, 62.5; H, 4.7; F, 9.9; N, 14.6%).

EXAMPLE 23

3-trans-p-Bromostyryl-4,5-dihydro-1,2,4-oxadiazole

80% yield, m.p. 178°–180° (decomp). (from ethanol), $\lambda_{max}$. (EtOH) 280 nm, ε 21500 (Found: C, 47.4; H, 3.6; Br, 31.3; N, 11.1. $C_{10}H_9BrN_2O$ requires C, 47.4; H, 3.6; Br, 31.5; N, 11.1%).

EXAMPLE 24

3-trans-p-Chlorostyryl-1,2,4-oxadiazole 3-trans-p-Chlorostyryl-4,5-dihydro-1,2,4-oxadiazole (1.043 g.) was dissolved in warm ethanol (30 ml.) and 6N-sulphuric acid (5 ml.) added. The solution was stirred at 0°–5°, when solid separated. Sodium nitrite (705 mg., 10.2 mM) in water (6 ml.) was added, dropwise and with stirring, during 11 min. The suspension was stirred at 0°–5° for 30 min. more (starch - KI test still positive). Water (5 ml.) was added and stirring continued for 30 min. more (faint starch - KI reaction). The mixture was cooled to 0° and the solid filtered off and washed with ice-cold 50% aqueous ethanol, then several times with water leaving 3-trans-p-chlorostyryl-1,2,4-oxadiazole (480 mg., 46.5%), m.p. 137°–138°.

EXAMPLE 25

3-trans-p-Azidostyryl-1,2,4-oxadiazole

Sodium nitrite (1.71 g.) in water (8 ml.) was added over 30 min. with stirring at 0° to 3-trans-p-aminostyryl-1,2,4-oxadiazole (4.0 g.) in glacial acetic acid (94 ml.) and 2N sulphuric acid (43 ml.). After a further 1 hr., urea was added to destroy excess of nitrous acid. Sodium azide (1.39 g.) in water (11 ml.) was added over 20 min. at 0° to the mechanically stirred diazonium-salt solution. The stirring was continued for a further 1.5 hr., the solution filtered, and the solid washed with water, and dried to leave the crude product (4.45 g.), m.p. 121°–122°. This product was extracted with ethyl acetate (100 ml.), the solution filtered, and the solvent removed to give 3-trans-p-azidostyryl-1,2,4-oxadiazole (4.31 g., 94.8%), m.p. 121°–122°, $\lambda_{max}$. (EtOH) 225, 298 nm, ε 14400, 30200 (Found: C, 56.15; H, 3.5; N, 32.9. $C_{10}H_7N_5O$ requires C, 56.3; H, 3.3; N, 32.85%).

EXAMPLE 26

3-trans-p-Bromostyryl-1,2,4-oxadiazole

Sodium nitrite (2.212 g.) in water (3 ml.) was added over 30 min. with stirring at 0° to 3-trans-p-aminostyryl-1,2,4-oxadiazole (4.97 g.) in glacial acetic acid (81 ml.) and 2N sulphuric acid (61 ml.). After a further 1.7 hr., urea was added to destroy the excess of nitrous acid. The cold solution was added over 30 min. to a stirred solution of cuprous bromide (4.36 g., freshly purified by washing with 2N hydrobromic acid) and potassium bromide (150 g.) in water (210 ml.). The solution was filtered after a further 1.5 hr., and the solid washed well with water and extracted with chloroform (100 ml.). The aqueous filtrate was extracted with chloroform (500 ml.) and the combined extracts were washed with saturated sodium hydrogen carbonate solution and dried. The chloroform solution was evaporated to dryness in vacuo and the residue chromatographed on silica gel (500 g.). Elution with 5% ethyl acetate-benzene gave 3-trans-p-bromostyryl-1,2,4-oxadiazole (4.31 g., 65%), m.p. 149°–149.5°, $\lambda_{max}$. (EtOH) 285 nm, ε 30500 (Found: C, 47.5; H, 2.8; N, 11.2. $C_{10}H_7BrN_2O$ requires C, 47.8; H, 2.8; N, 11.2%).

EXAMPLE 27

3-trans-p-Cyanostyryl-1,2,4-oxadiazole

Sodium nitrite (3.35 g.) in water (8.9 ml.) was added at 0°–5° during 25 min. to a stirred suspension of 3-trans-p-aminostyryl-1,2,4-oxadiazole (8.63 g.) in 2N hydrochloric acid (69 ml.). After 38 min. more, the excess of nitrous acid was destroyed with urea. Cuprous cyanide (4.53 g.) was dissolved in a solution of potassium cyanide (10.20 g.) in water (31 ml.), and stirred at 60° whilst the diazonium salt solution (also at 60°) was added during 30 min. The mixture was stirred at 70°–80° for 25 min., cooled, and filtered. The solid was washed with water until the washings were free of cyanide ion ($AgNO_3$ test) and dried to constant weight before extraction with boiling benzene (100 + 2 × 50 ml.). The combined extracts were treated with charcoal and filtered, and the benzene removed under reduced pressure to leave an orange solid (4.4 g.). This solid was dissolved in ethanol (250 ml.), the solution filtered, and the filtrate was evaporated to leave the crude nitrile (4.35 g., 48%), m.p. ca. 175°. Recrystallisation from ethanol gave 3-trans-p-cyanostyryl-1,2,4-oxadiazole (3.31 g., 37%), m.p. 179°–181° (decomp.). Sublimed at 130°/0.5 mm., it had m.p. 182°–183°, $\lambda_{max}$. (EtOH) 287–288 nm, $\epsilon$ 36000 (Found: C, 66.65; H, 3.6; N, 21.4. $C_{11}H_7N_3O$ requires C, 67.0; H, 3.6; N, 21.3%).

EXAMPLE 28

3-trans-p-Hydroxystyryl-1,2,4-oxadiazole

Sodium nitrite (2.8 g.) in water (12 ml.) was added over 45 min. with stirring at 0° to 3-trans-p-aminostyryl-1,2,4-oxadiazole (6.54 g.) in glacial acetic acid (154 ml.) and 2N sulfuric acid (70 ml.). After a further hour, urea was added to destroy excess of nitrous acid and this was followed by cupric sulphate pentahydrate (1.75 g.). 2N Sulphuric acid (20 ml.) was added and the solution heated at 52°–54° for 16 hr., and left at 25° for 24 hr. The solution was extracted consecutively with chloroform (250 ml.) and ethyl acetate (250 ml.). The extracts were washed with saturated sodium hydrogen carbonate solution and water. The acid solution was neutralised with sodium hydrogen carbonate and extracted with ethyl acetate (300 ml.) which was washed with water and combined with the other extracts. The combined extracts were dried and evaporated to dryness in vacuo. The residue was chromatographed on silica gel (600 g.). Elution with ethyl acetate-benzene (1:3) gave the hydroxy-compound (0.64 g., 9.4%) and a crude mixture (3.2 g., 47%). This mixture was rechromatographed on silica gel (600 g.) and eluted with ethyl acetate-benzene (1:9) to give 3-trans-p-hydroxystyryl-1,2,4-oxadiazole (1.71 g.), m.p. 128°–129°, $\lambda_{max}$. (EtOH) 226, 296 nm, $\epsilon$ 12800, 23500 (Found: C, 64.0; H, 4.45; N, 14.8. $C_{10}H_8N_2O_2$ requires C, 63.8; H, 4.3; N, 14.9%).

EXAMPLE 29

3-trans-p-Iodostyryl-1,2,4-oxadiazole

Sodium nitrite (2.224 g.) in water (6 ml.) was added over 30 min. with stirring at 0° to 3-trans-p-aminostyryl-1,2,4-oxadiazole (5.2 g.) in glacial acetic acid (122 ml.) and 2N sulphuric acid (56 ml.). After 1.5 hr. more, urea was added to destroy excess of nitrous acid. The solution was diluted with water (20 ml.) and added over 20 min. to a stirred mixture of potassium iodide (48.4 g.) and iodine (27 g.) in water (110 ml.) and chloroform (335 ml.). Stirring was continued for a further 1.3 hr., then the layers were separated, the aqueous layer extracted with chloroform (2 × 100 ml.), and the combined chloroform solutions washed with saturated sodium metabisulphite solution (100 ml.), saturated sodium hydrogen carbonate solution (100 ml.), and water. The chloroform was removed in vacuo and the residue was dissolved in methanol (50 ml.) and the solution filtered. The methanol was removed under reduced pressure, and the residue was treated with charcoal in chloroform. The solution was filtered and concentrated to ca. 20 ml. Crystals were deposited of 3-trans-p-iodostyryl-1,2,4-oxadiazole (3.03 g., 37%), m.p. 170°–171°, $\lambda_{max}$.(EtOH) 290 nm, $\epsilon$ 32950 (Found: C, 40.5; H, 2.6; N, 9.2. $C_{10}H_7IN_2O$ requires C, 40.3; H, 2.4; N, 9.4%).

EXAMPLE 30

3-trans-p-Thiocyanatostyryl-1,2,4-oxadiazole

Sodium nitrite (1.6 g.) in water (6 ml.) was added over 40 min. with stirring at 0° to 3-trans-p-aminostyryl-1,2,4-oxadiazole (3.74 g.) in glacial acetic acid (120 ml.) and 2N sulphuric acid (40 ml.). After 1.9 hr. more, excess of nitrous acid was destroyed with urea. This solution was added at 0° over 30 min. to a stirred solution of potassium thiocyanate (60 g.) and cuprous thiocyanate (6 g.) in water (20 ml.). The mixture was stirred for one hour at 0°–5° and left overnight to reach room temperature. The solution was treated with sodium hydrogen carbonate to bring the solution to pH 7–8 before extraction with chloroform (3 × 400 ml.). The extract was washed with saturated sodium hydrogen carbonate solution and water, and dried. The chloroform was removed in vacuo and the residue was recrystallized from aqueous ethanol to give 3-trans-p-thiocyanatostyryl-1,2,4-oxadiazole (2.7 g., 59%), m.p. 135°, $\lambda_{max}$. (EtOH) 286 nm, $\epsilon$ 32850 (Found: C, 57.8; H, 3.3; N, 18.1. $C_{11}H_7N_3OS$ requires C, 57.6; H, 3.1; N, 18.3%).

EXAMPLE 31 a. 3-(1,2-Dibromo-2-p-chlorophenylethyl)-1,2,4-oxadiazole

Bromine (0.5 ml.) in chloroform (25 ml.) was slowly added at room temperature to a stirred solution of 3-trans-p-chlorostyryl-1,2,4-oxadiazole (500 mg.) in chloroform (25 ml.). After 2 hours, the solution was washed with aqueous sodium bisulphite solution, then with 2N sodium carbonate solution, and finally with water. Removal of the chloroform and recrystallisation from aqueous methanol of the residue gave fine needles of 3-(1,2-dibromo-2-p-chlorophenylethyl)-1,2,4-oxadiazole (818 mg., 92%), m.p. 141°–142°, $\lambda_{max}$. (EtOH) 268 nm, $\epsilon$ 8900 (Found: C, 32.9; H, 2.1; N, 7.6; Br + Cl, 53.4. $C_{10}H_7Br_2ClN_2O$ requires C, 32.8; H, 1.9; N, 7.65; Br +Cl, 53.3%).

b. 3-($\alpha$- or $\beta$-Bromo-p-chlorostyryl)-1,2,4-oxadiazole 3-(1,2-Dibromo-2-p-chlorophenylethyl)-1,2,4-oxadiazole (350 mg.) was dissolved in dry ether (20 ml.), and a solution of 1,5-diazabicyclo[4,3,0]non-5-ene (210 mg.) in dry ether (10 ml.) added dropwise with stirring. An immediate precipitate was formed. The mixture was poured into 2N sulphuric acid (10 ml.) and the ether separated and washed with water and dried ($Na_2SO_4$). Removal of the ether in vacuo left a colourless, low-melting product (245 mg., 90%) which was recrystallized from ethanol to give colourless crystals of 3-($\alpha$- or $\beta$-bromo-p-chlorostyryl)-1,2,4-oxadiazoles (150 mg., 55%), m.p. 98°–100°, $\lambda_{max}$. (EtOH) 268 nm, $\epsilon$ 12760 (Found: C, 42.1; H, 2.2; N, 9.5; Br + Cl, 40.1. $C_{10}H_6BrClN_2O$ requires C, 42.1; H, 2.1; N, 9.8; Br + Cl, 40.4%).

EXAMPLE 32

3-trans-p-Methylsulphinylstyryl-1,2,4-oxadiazole

Aqueous hydrogen peroxide solution (0.84 ml., 29% w/v) was added over 10 min. with stirring at 10° to 3-trans-p-methylthiostyryl-1,2,4-oxadiazole (2.18 g.) in glacial acetic acid (20 ml.) and acetic anhydride (20 ml.). The mixture was left to reach room temperature over 4 hr. and more hydrogen peroxide solution (0.1 ml.) then added. The mixture was left overnight, then poured slowly into water (300 ml.) and all the solvent evaporated under reduced pressure to leave 3-trans-p-methylsulphinylstyryl-1,2,4-oxadiazole (2.22 g., 95%), m.p. 146°–147°, $\lambda_{max}$. (EtOH) 287 nm, $\epsilon$ 28800 (Found: C, 56.3; H, 4.7; N, 11.6. $C_{11}H_{10}N_2O_2S$ requires C, 56.4; H, 4.3; N, 12.0%).

EXAMPLE 33

3-trans-p-Methylsulphonylstyryl-1,2,4-oxadiazole

Aqueous hydrogen peroxide solution (1.61 ml., 29% w/v), was added with stirring to 3-trans-p-methylthiostyryl-1,2,4-oxadiazole (1.42 g.) in glacial acetic acid (15 ml.) and acetic anhydride (15 ml.). The mixture was kept at 20° for 1 hr., and at 38° for 4 hr. before evaporation of the solvent and washing of the residue with water. The solid was dried, leaving 3-trans-p-methylsulphonylstyryl-1,2,4-oxadiazole (1.6 g., 98%), m.p. 194°–196°, $\lambda_{max}$. (EtOH) 274 inflexion, 283.5 nm, $\epsilon$ 25500, 26740 (Found: C, 52.5; H, 4.1; N, 10.9. $C_{11}H_{10}N_2O_3S$ reqires: C, 52.8; H, 4.0; N, 11.2%).

EXAMPLE 34

3-trans-p-Chlorostyryl-1,2,4-oxadiazole

Phosphoryl chloride (0.94 ml.) dissolved in anhydrous ether (5 ml.) was added to a solution of dimethylformamide (0.77 ml.) in anhydrous ether (5 ml.) and allowed to stand until a colourless oil had separated. The ether was decanted and the oil washed by decantation with anhydrous ether. The oil was dissolved in tetrahydrofuran (10 ml.), cooled to 0° and a solution of p-chlorocinnamamidoxime monohydrate (0.98 g.) in tetrahydrofuran (10 ml.) at 0° was added. After 1 hr. the solution was poured into water (250 ml.), the precipitated solid (0.67 g.) was collected and crystallized from methanol (10 ml.) to give 3-trans-p-chlorostyryl-1,2,4-oxadiazole (0.51 g., 54.1%) m.p. 129°.

EXAMPLE 35

3-trans-p-Chlorostyryl-1,2,4-oxadiazole p-Chlorocinnamamidoxime monohydrate (1.08 g., 5 mmole.) was refluxed in chloroform and the water was removed azeotropically. The chloroform was removed under reduced pressure, and anhydrous formamide (225 mg., 5 mmole.) was added. The mixture was heated in an oil-bath at 170°–175° for 10 min. The residual dark oil was chromatographed in benzene on silica, giving crude 3-trans-p-chlorostyryl-1,2,4-oxadiazole, 201 mg. (19%), m.p. 130°–135°. Recrystallization from methanol gave pure 3-trans-p-chlorostyryl-1,2,4-oxadiazole, m.p. and mixed m.p. 134°–135°, identical (infrared spectrum and thinlayer chromatography) with the compound previously described.

EXAMPLE 36 trans-5-Methyl-3-p-methylsulphinylstyryl-1,2,4-oxadiazole

Hydrogen peroxide (ca 29% w/v, 0.30ml) was added in portions during 2.4 hr to a stirred solution of trans-5-methyl-3p-methylthiostyryl-1,2,4-oxadiazole (464 mg) in glacial acetic acid (5 ml.) and acetic anhydride (5 ml.) at 5°–15° C and the mixture left at room temperature for 16 hrs. More hydrogen peroxide (0.1 ml.) was added during 3 hrs. The solution was evaporated to dryness under reduced pressure and water (10 ml.) added giving the title compound (403 mg., 81%), m.p. 176°–177° C, $\lambda$ max (EtOH) 289 nm, ($\epsilon$ 31,600) (Found, after sublimation, C, 57.75, H, 4.8; N, 11.6. $C_{12}H_{12}N_2O_2S$ requires C, 58.0; H, 4.9; N, 11.3%).

EXAMPLE 37 trans-5-Methyl-3-p-methylthiostyryl-1,2,4-oxadiazole p-Methylthiocinnamamidoxime (1.24 g) was refluxed in acetic anhydride (10 ml.) for 2 hr. The mixture was evaporated to dryness under reduced pressure, and water (10 ml) was added. The solid was filtered off and recrystallized (charcoal) from aqueous methanol to give the title compound (0.43 g., 31%), m.p. 112°–113° C, $\lambda$ max (EtOH) 236, 320 nm. ($\epsilon$ 11,600, 28,400) (Found: C, 62.0; H, 5.1; N, 12.1; $C_{12}H_{12}N_2OS$ requires C, 62.0; H, 5.2; 12.1%).

EXAMPLE 38 trans-5-Ethyl-3-p-methylthiostyryl-1,2,4-oxadiazole.

A mixture of trans-p-methylthiocinnamamidoxime (2.08 g., 10 mM) and propionic anhydride (2.25 ml) was heated at 100° C for 2 hr., and then poured into aqueous 2N. sodium bicarbonate solution (50 ml). After ca. 30 minutes the mixture was extracted with chloroform (2 × 20 ml), and the combined extracts were washed with water (2 × 10 ml.) and were dried ($MgSO_4$). The filtered solution was evaporated to give a crude product (2.32 g., 94%) as a brown crystalline solid. Chromatograhic purification on silica gel (250g.) using chloroform as eluant, gave trans-5-ethyl-3-p-methylthiostyryl-1,2,4-oxadiazole (1.65g., 67%) as pale yellow needles, m.p. 47° – 48° C [Found (on a sublimed sample, m.p. 48° C): C, 63.5; H, 5.9; N, 11.7; S, 13.0. $C_{13}H_{14}N_2OS$ requires C, 63.4; H, 5.7; N, 11.4; S, 13.0], $\lambda_{max}$ 236 and 323nm. ($\epsilon$ 11,720 and 27,590), $\nu_{max}$. 1650, 1590, 972 and 814 cm$^{-1}$. The p.m.r. spectrum showed (i) multiplets at $\tau$ 2.53 and $\tau$ 2.80 (ArH), (ii) doublets at $\tau$ 2.38 and $\tau$ 3.04 (J=16c/s) (trans CH=CH), (iii) a quartet at $\tau$ 7.08 ($CH_3$-$CH_2$-), (iv) a singlet at $\tau$ 7.51 ($CH_3$-S) and (v) a triplet at 8.58 ($CH_3$-$CH_2$-).

EXAMPLE 39 trans-5-Ethyl-3-p-methylsulphinylstyryl-1,2,4-oxadiazole.

Aqueous hydrogen peroxide (0.15 ml., 27.9% w/v, 0.12 mM) was added to a solution of 5-ethyl-3-p-methylthiostyryl-1,2,4-oxadiazole (246 mg., 1 mM) in acetic anhydride (1 ml.) and glacial acetic acid (1 ml.) and the mixture was stirred at room temperature for 1 hr. The solution was poured into 2N sodium bicarbonate solution (20ml) with stirring. After 30 minutes, the white precipitate was filtered off, wahsed with water (2 ml) and was dried, to give trans-5-ethyl-3-p-methylsulphinylstyryl-1,2,4-oxadiazole (198 mg., 76%), m.p. 97° – 99° C [Found (on a sublimed sample, m.p. 99°–100° C): C, 59.2; H, 5.4; N, 10.7; S, 12.2. $C_{13}H_{14}N_2O_2S$ requires C, 59.5; H, 5.4; N, 10.7; S, 12.2], $\lambda_{max}$ 290 and 221 nm ($\epsilon$ 31,690 and 12,990 respectively), $\nu_{max}$ 1046 (sulphoxide), 974 and 818cm$^{-1}$. The p.m.r. spectrum showed (1) a multiplet at γ 2.30 (Ar-H), (ii) doublets at τ 2.23 and τ 2.88 (J=16 c/s) (trans CH=CH) (iii) a quartet at τ 7.02 (CH$_3$-CH$_2$-), (iv) a singlet at τ 7.22 (CH$_3$-S-O), (v) a triplet at τ 8.56 (CH-CH$_2$-).

EXAMPLE 40 trans-5-Ethyl-3-p-methylsulphonylstyryl-1,2,4-oxadiazole.

Aqueous hydrogen peroxide (0.6ml., 27.9% w/v. 5mM) was added to a solution of 5-ethyl-3-p-methylthiostyryl-1,2,4-oxadiazole (246 mg., 1 mM) in acetic anhydride (2ml) and glacial acetic acid (2ml), and the mixture was stirred at 38° C for 15 hr. The solution was poured into aqueous 2N sodium bicarbonate (50 ml). After 30 minutes, the white precipitate was filtered off, washed with water (5ml), and was dried, to give trans-5-ethyl-3-p-methylsulphonylstyrl-1,2,4-oxadiazole (237 mg., 85%), m.p. 127°–128° C [Found: (on a sublimed sample, m.p. 126°–128° C): C, 56.2; H, 4.9; N. 9.6; S, 11.5. $C_{13}H_{14}N_2O_3S$ requires C, 56.1; H, 5.0; N. 10.1; S, 11.5], $\lambda_{max}$ 286 nm (ε 34,500), $\nu_{max}$(CS$_2$) 1330, 1160 (sulphone) and 960cm$^{-1}$. The p.m.r. spectrum showed (i) multiplets at τ 2.03 and 2.33 (Ar -H), (ii) doublets at τ 2.27 and τ 2.85 (trans CH=CH), (iii) a singlet at τ 6.91 (CH$_3$-SO$_2$-), (iv) a quartet at τ 7.02 (CH$_3$-CH$_2$-), (v) a triplet at τ 8.53 (CH$_3$-CH$_2$-).

EXAMPLE 41 trans-5-Methyl-3-p-methylthiostyryl-4,5-dihydro-1,2,4-oxadiazole.

Freshly distilled acetaldehyde (4.0ml., 70 mM) was added to a solution of p-methylthiocinnamamidoxime (2.08g., 10mM) in dioxan (20 ml) and water (20ml), and the mixture was stirred at 90° C under reflux for 3 hr., and then kept at 0° C overnight. The precipitate was filtered off, washed with cold methanol (5ml), and was dried, to give trans-5-methyl-3-p-methylthiostyryl-4,5-dihydro-1,2,4-oxadiazole (1.80g., 78%) as a cream-coloured crystalline solid m.p. 154–155° C (Found: C 61.3; H, 6.0; N, 11.4; S, 13.7; $C_{12}H_{14}N_2OS$ requires C, 61.5; H, 6.0; N, 11.9; S, 13.7), $\lambda_{max}$ 236 and 328 nm (ε 13,140 and 26,700 respectively), $\nu_{max}$ 3300 (NH), 960 and 805 cm$^{-1}$ The p.m.r. spectrum (CDCl$_3$ + DMSO d$^6$) showed (i) multiplets at τ 2.60 and τ 2.82 (AR-H), (ii) doublets at τ 2.95 and τ 3.44 (trans CH=CH), (iii) a broad singlet at τ 4.05 (NH), (iv) a multiplet at τ 4.25 (CH$_3$-CH-), (v) a singlet at τ 7.60 (CH$_3$-S-), and (vi) a multiplet at τ 8.50 (CH$_3$-CH-).

EXAMPLE 42 trans-3-p-Methylthiostyryl-5-trichloromethyl-1,2,4-oxadiazole. Redistilled trichloroacetyl chloride (21.2g., 0.12M) was added dropwise at room temperature to a stirred suspension of p-methylthiocinnamamidoxime (10.4g., 0.05M) in chloroform (150ml) and dry pyridine (10ml). After 1 hr., the solution was evaporated to dryness, and the residue in chloroform was chromatrographed on silica gel (400g). The eluate was evaporated to dryness and the crude product was crystalised from ethanol to give trans-3-p-methylthiostyryl-5-trichloromethyl-1,2,4-oxadiazole (12.0g., 71%) as pale golden needles, m.p., 111°–113° C (Found: C, 43.0; H, 2.8; N, 8.5; S, 9.6; Cl, 31.3%. $C_{12}H_9Cl_3N_2OS$ requires C, 42.9; H, 2.7; N, 8.4; S, 9.6; Cl, 31.8%), $\lambda_{max}$ 240 and 331 nm (ε 12,280 and 30, 600), $\nu_{max}$. 970 and 745 cm$^{-1}$ (Cl$_3$C). The p.m.r. spectrum showed (i) multi-plets at τ 2.56 and τ 2.82 (Ar-H), (ii) doublets at τ 2.32 and τ 3.11 (J=16c/s) (trans CH=CH), and (iii) a singlet at τ 7.52 (CH$_3$-S-).

EXAMPLE 43 trans-3-p-Methylsulphonylstyryl-5-trichloromethyl-1,2,4-oxadiazole

A solution of trans-3-p-methylthiostyryl-5-trichloromethyl-1,2,4-oxadiazole (1.007g., 3mM) in glacial acetic acid (18 ml) and acetic anhydride (9 ml) was treated with 40% peracetic acid (0.70ml., 9mM) at room temperature. After 18 hours, the solution was diluted with ethanol and evaporated to dryness. The residue was taken up in ethanol, and the solution again evaporated to dryness. Ethanol (5ml) was added, and the product was filtered off and dried, to give trans-3-p-methylsulphonylstyryl-5-trichloromethyl-1,2,4-oxadiazole (0.814 g., 74%) as a cream-coloured solid, m.p. 147°–148° [Found: C, 39.3; H, 2.5; Cl, 28.9; N, 7.3; S, 8.5%. $C_{12}H_9Cl_3N_2O_3S$ requires C, 39.2; H, 2.5; Cl, 29.0; N, 7.6; S, 8.7%], $\nu_{max}$. (Nujol) 1305 and 1140 (sulphone), and 960cm$^{-1}$, $\lambda_{max}$ 285 nm. (ε 33,800).

The p.m.r. spectrum (DMSO d$^6$) showed (i) multi-plets at τ 1.82 and τ 2.06 (Ar-H), (ii) doublets at τ 2.04 and τ 2.42 (J=17c/s.) (trans CH=CH), and (iii) a singlet at τ 8.70 (CH$_3$-SO$_2$).

EXAMPLE 44

5-Methyl-3-trans-p-methylsulphonylstyryl-1,2,4-oxadiazole

An aqueous solution of hydrogen peroxide (0.35 ml., 29% w/v; 3mM) was added to a solution of 5-methyl-3-trans-p-methylsulphinylstyryl-1,2,4-oxadiazole (200 mg., 0.8 mM) in glacial acetic acid (3 ml.) and acetic anhydride (3 ml.) at room temperature. After 48 hours the mixture was poured into water and the resulting precipitate was filtered off and dired to give the title compound (153 mg., 72%) m.p. 188°–190° C [Found: C, 53,9; H, 4.7; N, 10.2. $C_{12}H_{12}N_2O_3S$ (264.3) requires C, 54.5; H 4.6; N, 10.6%]. $\lambda_{max}$. . 278 (inflex.), 284 nm(ε 30,700, 32,000) $\lambda_{max}$. (Nujol) 1145, 1295 cm$^{-1}$.

EXAMPLE 45

5-Amino-3-trans-p-methylthiostyryl-1,2,4-oxadiazole

A mixture of 3-trans-p-methylthiostyryl-5-trichloromethyl1,2,4-oxadiazole (3.357 g., 10 mM) and liquid ammonia (100 ml.) was stirred for 3 hours and the ammonia was then allowed to evaporate. The residue was crystallised from chloroform (charcoal) to give 5-amino-3-trans-p-methylthiostyryl-1,2,4-oxadiazole (2.29 g., 98%) as colourless plates, m.p. 199°–200° C. $\nu_{max}$. (Nujol) 3450 cm$^{-1}$ (NH$_2$). The N.M.R. spectrum (DMSO d$^6$) showed a singlet (3H) at 7.50 τ(-S-CH$_3$); a doublet (1 H) at 3.12 τ(J=16 c/s.) (trans CH = CH); a doublet (1 H) at 2.55 τ(J = 16 c/s) (trans CH = CH); a multiplet (4H) at 2.38 τ–2.76 τ (Ar -H); and a singlet (2H) at 2.25 τ(NH$_2$).

EXAMPLE 46

5-Amino-3-p-methylsulphinylstyryl-1,2,4-oxadiazole

Aqueous hydrogen peroxide solution (1.7 ml., 27.8% w/v; 14 mM) was added to a stirred suspension of 5-amino-3-p-methylthiostyryl-1,2,4-oxadiazole (4.00 g., 17.16 mM) in glacial acetic acid (200 ml.) at room temperature. After 6 hours the clear solution was evaporated to dryness and the residue washed thoroughly with ethanol to give the title compound (3.40 g., 80%), m.p. 270°–272° C. (Found C, 52.5; H, 4.48; N, 17.1; S, 13.0. $C_{11}H_{11}N_3O_2S$ requires C, 53.0; H, 4.45; N, 16.9; S, 12.9%). $\lambda_{max}$. (EtOH) 288 nm ($\epsilon$ 29,200), $\nu_{max}$. (Nujol) 3350, 3250, 1036 cm$^{-1}$.

EXAMPLE 47

5-Amino-3-p-methylsulphonylstyryl-1,2,4-oxadiazole

A mixture of aqueous hydrogen peroxide (0.40 ml., 27.8% w/v; 3.28 mM) and 5-amino-3-p-methylthiostyryl-1,2,4-oxadiazole (233 mg., 1 mM) in glacial acetic acid (10 ml.) was stirred at room temperature for 3 days, and finally at 40° C for 10 minutes. The solution was evaporated to dryness, and the residue was washed thoroughly with ethanol and dried to give the title compound (216 mg., 82%), m.p. 286°–287° C. (Found C, 50.0; H, 4.2; N, 15.3; S, 12.1. $C_{11}H_{11}N_3O_3S$ requires C, 49.8; H, 15.8; S. 12.1%) $\lambda_{max}$. (EtOH) 278 nm ($\epsilon$ 28,100), $\nu_{max}$. (Nujol) 3350 3270, 1298, 1142 cm$^{-1}$.

EXAMPLE 48

3-trans-β-(5-Chlorothien-2-yl)vinyl-1,2,4-oxadiazole.

A mixture of 3-(5-chlorothien-2-yl)acrylamidoxime (608 mg., 3mM), triethyl orthoformate (3.0 ml.) and boron trifluoride etherate (1 drop) was heated at 90° for 10 min., and was evaporated to give a yellow solid. Crystallisation from petrol (60°–80°) give the title oxadiazole (485 mg., 76%) as pale yellow needles, m.p. 85°, [Found: C, 45.1; H, 2.5; Cl, 16.8; N, 13.5; S, 15.4. $C_8H_5ClN_2OS$ (212.7) requires C, 45.2; H, 2.4; Cl, 16.7; N, 13.2; S, 15.1%]. $\lambda_{max}$. 314 nm ($\epsilon$ 23,650), $\nu_{max}$. (CHBr$_3$) 960 cm.$^{-1}$ (trans CH=CH).

EXAMPLE 49

3-trans-β-(5-Chlorothien-2-yl)vinyl-1,2,4-oxadiazole.

A solution of sodium ethoxide (containing ca. 3g. sodium) in dry ethanol (200ml.) was added dropwise under dry nitrogen to a stirred solution of 2-chloro-5-formylthiophene (14.65 g., 0.1M) and (1,2,4-oxadiazol-3-yl) methyl phosphonium chloride (38.08g., 0.1M) in dry ethanol (1 l.) containing a trace of phenolphthalein. Addition was continued until the pink colouration persisted. The mixture was stirred for a further 30 min. and was filtered. The salt was washed with ethanol (100 ml.), and the combined filtrates were evaporated to dryness. The residue was extracted with hot petrol (60°–80°) (6 × 200 ml.), the combined solutions were evaporated, and the residue was chromatographed on silical gel (400g.) using chloroform as eluant. The fraction containing the oxadiazole was evaporated to dryness, and the residue (18.18g., 85.5%) was crystallised from petrol to give the crude product as colourless needles, m.p. 75°–78° (35% cis, 65% trans).

A solution of the mixture (11.70g., 55mM) in benzene (400 ml.) containing a crystal of iodine was heated under reflux for 20 hr. The cooled solution was washed with aqueous sodium thiosulphate until colourless, and then with water, and was dried (MgSO$_4$). The solvent was removed, and the residue was crystallised from petrol to give 3-trans-β-(5-chlorothien-2-yl)vinyl-1,2,4-oxadiazole (6.94g., 59%) as colourless needles, m.p. 86°–88°,

EXAMPLE 50 trans-3-p-Methylsulphinylstyryl-1,2,4-oxadiazole.

trans-p-Methylsulphinylcinnamamidoxime (558 mg.) was suspended in dry ether (30ml.) containing redistilled triethylamine (5ml.) at −40°, stirred and treated with an excess formyl fluoride (ca. 1.5 ml., at −65°). The temperature was allowed to warm from −40° to −10° over a period of 1 hour. Stirring was then continued overnight at room temperature. After standing for 64 hours the pale yellow sticky precipitate was distributed between ethyl acetate and 2N-hydrochloric acid. The upper layer was washed successively with a solution of sodium hydrogon carbonate and water, dried and concentrated to give the title compound as crystals (0.32 g., 56%) $\nu_{max}$ Nujol 812 (p-C$_6$H$_4$), 972 (trans CH=CH), 1050 cm$^{-1}$ (S → O) and 0.38τ (d = 17 cps., trans CH=CH). 7.18τ (CH$_3$) for a soltuion in (CD$_3$)$_2$SO.

EXAMPLE 51 trans-3-o-Nitrostyryl-1,2,4-oxadiazole.

o-Nitrocinnamamidoxime (1.84 g.) was refluxed for 1 hr. in ethyl orthoformate (15 ml.) containing boron trifluoride etherate (4 drops). The mixture was refrigerated overnight and filtered to give trans-3-o-nitrostyryl-1,2,4-oxadiazole (1.24 g., 64%), m.p. 128°. Evaporation of the filtrate gave an additional 0.51 g. (26%) of the title compound. A sample recrystallised from aqueous acetone has m.p. 120°–121°, $\lambda_{max}$. 247 nm, $\epsilon$ 18900 (Found: C, 55.2; H, 3.3; N, 19.4. $C_{10}H_7N_3O_3$ requires C, 55.3; H, 3.25; N, 19.35%).

EXAMPLE 52 trans-3-o-Aminostyryl-1,2,4-oxadiazole.

Titanous chloride solution (15% w/v, 380 ml.) was added during 25 min. to a stirred solution of 3-o-nitrostyryl-1,2,4-oxadiazole (10.85 g.) in acetone (1 litre). After 30 min. more, the acetone was removed, and solid sodium hyrdogen carbonate was added to the stirred solution until the pH was 6–7. The mixture was extracted thoroughly with ethyl acetate solution was washed with water, then dried (MgSO$_4$) and evaporated, leaving trans-3-o-aminostyryl-1,2,4-oxadiazole (7.5 g., 80%), m.p. 108°–109°, $\lambda_{max}$. 240, 280–281, 350 nm, $\epsilon$ 14000, 12800, 6200 [Found (after sublimation): C, 64.2; H, 5.2; N, 22.1 $C_{10}H_9N_3O$ requires C, 64.2; H, 4.85; N, 22.45%].

EXAMPLE 53 trans-3-o-Thiocyanatostyryl-1,2,4-oxadiazole.

trans-3-o-Aminostyryl-1,2,4oxadiazole (374 mg.) in glacial acetic acid (12 ml.) and 2N-sulphuric acid (4 ml.) was diazotised with sodium nitrite (160 mg.) in water (1 ml.), and the diazonium solution was added at 0°–5° to a stirred solution of freshly prepared cuprous thiocyanate (1.0 g.) and potassium thiocyanate (6 g.) in water 2 ml.). The solution was stirred for 18 hr. then sodium hydrogen carbonate solution was added until the pH was 6. The thiocyanate was isolated with the aid of ethyl acetate, then purified by extraction with chloroform and filtration, to give crystals, m.p. 101°–102°. Crystallisation from aqueous methanol gave the thiocyanate, (354 mg., 77%), m.p. 101°–102°. Recrystallisation from aqueous methanol gave trans-3-o-thiocyanatostyryl-1,2,4-oxadiazole, m.p. 107°–108°, $\lambda_{max}$. 276 nm, $\epsilon$ 21000 (Found C, 57.3; H, 3.3; N, 17.9 $C_{11}H_7N_3OS$ requires C, 57.6; H, 3.1; N, 18.3%).

EXAMPLE 54 trans-3-o-Methylthiostyryl-1,2,4-oxadiazole.

3-o-Thiocyanatostyryl-1,2,4-oxadiazole (229 mg.) and trimethyl phosphite (0.12 ml.) were mixed and heated to 70°, then kept at 70°–80° for 10 min. The mixture was evaporated and the residue was chromatographed on a thick silica plate (20 × 20 cm.). The band of highest $R_F$ was eluted (ethyl acetate) to give trans-3-o-methylthiostyryl-1,2,4-oxadiazole (55 mg., 25%), m.p. 56°–58°, $\lambda_{max.}$ 254, 278, 332 nm, $\epsilon$ 14600, 13700, 2400 [Found (after sublimation): C, 60.8; H, 5.0; N, 12.8. $C_{11}H_{10}N_2OS$ requires C, 60.5; H, 4.6; N, 12.8%].

EXAMPLE 55 trans-3-o-Methylsulphinylstyryl-1,2,4-oxadiazole.

trans-3-o-Methylthiostyryl-1,2,4-oxadiazole (0.660 g.) was suspended in a mixture of glacial acetic acid (6.65 ml.) and acetic anhydride (6.05 ml.). The suspension was stirred at 10° and hydrogen peroxide (29% w/v, 0.15 ml.) was added during 45 min. The mixture was refrigerated overnight, then poured into water (91 ml.), and left at 0° for 30 min., then evaporated to dryness. The residue was separated chromatographically on a thick silica plate (20 × 40 cm.) in benzene and the band of $R_F$ 0.21 was eluted, giving the crude sulphoxide as a gum (0.349 g.). Recrystallisation from acetone, then from ethyl acetate - light petroleum (b.p. 40°–60°) gave trans-3-o-methylsulphinylstyryl-1,2,4-oxadiazole (0.165 g., 24%), m.p. 135°–138°, $\lambda_{max.}$ (EtOH) 279 nm, $\epsilon$ 18500, $\nu_{max.}$ (nujol) 1032 cm.$^{-1}$ (S → O), (Me$_2$SO, d$^6$) 0.40 (CH), 1.8 – 2.7 (aromatic + trans-CH=CH), 7.25 (Me) [Found (after sublimation): C, 57.2; H, 4.5; N, 11.3. $C_{11}H_{10}N_2O_2S$ requires C, 56.4; H, 4.3; N, 12.0%].

EXAMPLE 56 trans-3-m-Nitrostyryl-1,2,4-oxadiazole.

Prepared analagously to Example 51 m.p. 144°–146° (from aqueous methanol), $\lambda_{max.}$ (EtOH) 263 nm, $\epsilon$ 33700 [Found (after sublimation); C, 55.6; H, 3.5; N, 19.4. $C_{10}H_7N_3O_3$ requires C, 55.3; H, 3.25; N, 19.35%].

EXAMPLE 57 trans-3-m-Aminostyryl-1,2,4-oxadiazole.

Prepared analagously to Example 52 m.p. 122°–124° (from aqueous methanol), $\lambda_{max.\,(EtOH)}$ 251–254, 281, 332 nm, $\epsilon$ 23000, 21000, 3130 [Found (after sublimation): C, 64.1; H, 4.8; N, 22.2 $C_{10}H_9N_3O$ requires C, 64.2; H, 4.85; N, 22.4%].

EXAMPLE 58 trans-3-m-Thiocyanatostyryl-1,2,4-oxadiazole.

Prepared analagously to Example 53 m.p. 112°–113.5° (from aqueous ethanol), $\lambda_{max.}$ (EtOH) 238, 274 nm, $\epsilon$ 19500, 24900 [Found (after sublimation): C, 57.9; H, 3.3; N, 18.0 $C_{11}H_7N_3OS$ requires C, 57.6; H, 3.1; N, 18.3%].

EXAMPLE 59 trans-3-m-Methylthiostyryl-1,2,4-oxadiazole.

Prepared analogously to Example 54 (heating was at 130° for 20 min.), 62°, $\lambda_{max.}$ (EtOH) 261 nm, $\epsilon$ 34500

EXAMPLE 60 trans-3-m-Methylsulphinylstyryl-1,2,4-oxadiazole.

trans-3-m-Methylthiostyryl-1,2,4-oxadiazole (600 mg.) was suspended in a mixture of glacial acetic acid (5.6 ml.) and acetic anhydride (5.6 ml.). The suspension was stirred at 0° and hydrogen peroxide (29% w/v, 0.30 ml.) was added in 3 portions of hourly intervals. The solution was refrigerated overnight and poured into water (100 ml.), then left at 0° for 1 hr. and evaporated to dryness. The residue was separated chromatographically on 2 thick silica plates (20 × 40 cm.) in ethyl acetate, and the band of $R_F$ 0.34 was eluted, giving the sulphoxide (453 mg., 70%), m.p. 130–133°. Sublimation of a portion gave trans-3-m-methylsulphinylstyryl-1,2,4-oxadiazole, m.p. 130° –133° $\lambda_{max.}$ (EtOH) 273 nm, $\epsilon$ 26500 (Found: C, 56.5; H, 4.3; N, 11.6. $C_{11}H_{10}N_2O_2S$ requires C, 56.4; H, 4.3; N, 12.0%).

EXAMPLE 61 trans-3-p-Methylthiostyryl-4,5-dihydro-1,2,4-oxadiazole.

Aqueous formaldehyde (4.0 ml., 39% w/v, 52 mmole) was added to a solution of p-methylthiocinnamidoxime (2.08 g., 10 mmole) in dioxan (20 ml.) and water (20 ml.), and the mixture was stirred at 90° for 2 hr., and was then kept at 0° overnight. The resulting precipitate was filtered off, washed with cold methanol (5 ml.) and was dried, to give trans-4,5-dihydro-3-p-methylthiostyryl-1,2,4-oxadiazole (1.37 g., 62%), m.p. 154°–156°, $\lambda_{max.}$ 236, 327 nm, ($\epsilon$ 12470, 25990) [Found: C, 60.0; H, 5.7; N, 12.4; S, 14.2. $C_{11}H_{12}N_2OS$ (220.3) requires C, 60.0; H, 5.5; N, 12.7%; S, 14.5%].

EXAMPLE 62 cis-3-p-Methylsulphinylstyryl-1,2,4-oxadiazole and cis-3-p-Methylsulphonylstyryl-1,2,4-oxadiazole.

A solution of trans-3-p-methylsulphinylstyryl-1,2,4-oxadiazole (3.5 g.) in absolute ethanol (3.5 l.) was irradiated with UV light (maximum emission ca. 350 nm) for a total of 35 hr. The solution was evaporated to a volume of ca. 50 ml., and was kept at 0° overnight. Colourless needles (736 mg.), m.p. 154°–155°, of the trans-sulphoxide were filtered off, and the filtrate was reduced further in volume. A second crop (178 mg.), m.p. 153°–154°, of the trans-sulphoxide was collected, and after further evaporation and refrigeration of the filtrate, a third crop (166 mg.) m.p. 152°–154°, was obtained. The filtrate was evaporated to give a light brown oil (2.787 g., 80%), and a portion (2.182 g.) was chromatographed on silica (200 g.) using chloroform as eluant. An initial fraction yielded cis-3-p-methylsulphonylstyryl-1,2,4-oxadiazole (407 mg., 12%), m.p. 76°–79°, $\lambda_{max.}$ 273, 281 (infl.) nm, ($\epsilon$ 17000, 15630).

The column was then eluted with chloroform - ethyl acetate (1:1 v/v), and the eluate was evaporated to give a yellow oil, which partially crystallized. Crystals of the trans-sulphoxide (86 mg.) m.p. 148°–150°, were filtered off, and were washed with ethanol (1 ml.) The combined filtrates were evaporated to give cis-3-p-methylsulphinylstyryl-1,2,4-oxadiazole (1.294 g., 37%) as a light brown oil, $\lambda_{max.}$ 278 nm, ($\epsilon$ 15,000).

EXAMPLE 63

3-trans-β-(5-Methylthiothien-2-yl)vinyl-1,2,4-oxadiazole.

A mixture of 3-(5-methylthiothien-2-yl) acrylamidoxime (6.8 g., 34.7 mmole), triethylorthoformate (50 ml.) and boron trifluoride etherate (3 drops) was heated at 100° for 1 hr. The solution was evaporated to dryness, and the residue was crystallised from petrol to give the oxadiazole (3.69 g., 52%) as orange needles, m.p. 58°–58.5° [Found: C, 47.9; H, 3.5; N, 12.8; S, 28.8. $C_9H_8N_2OS_2$ requires C, 48.2; H, 3.6; N, 12.5; S, 28.6%] $\lambda_{max.}$242, 257, 337 nm ($\epsilon$ 6260, 6080, 15280), $\lambda_{max.}$(CHBr$_3$) 1640, 958 cm.$^{-1}$.

EXAMPLE 64

3-trans-β-(5-Methylsulphinylthien-2-yl)vinyl-1,2,4-oxadiazole.

Peracetic acid (0.42 ml., 40% w/v; 2.23 mmole) was added to a solution of 3-trans-β-(5-methylthiothien-2-yl)vinyl-1,2,4-oxadiazole (500 mg., 2.23 mmole) in glacial acetic acid (10 ml.) at 0°. After 10 min. ethanol was added, and the solution was evaporated to dryness. The residue was crystallised from aqueous ethanol to give the sulphoxide (345 mg., 64%) as yellow needles, m.p. 123°–125° [Found: C, 44.2; H, 3.3; N, 11.8; S, 26.8. $C_9H_8N_2O_2S_2$ (240.3) requires C, 45.0; H, 3.4; N, 11.7; S, 26.7%]. $\lambda_{max}$.315 nm, ($\epsilon$ 25700), $\nu_{max}$.(CHBr$_3$) 1040, 968 cm.$^{-1}$.

EXAMPLE 65 trans-5-Methyl-3-p-nitrostyryl-1,2,4-oxadiazole.

A suspension of p-nitrocinnamamidoxime (20.7 g.) in acetic anhydride (70 ml.) was heated on a steam-bath for one hour when solution occurred. The cooled solution was neutralized with saturated sodium carbonate solution and the precipitated solid filtered off, washed with water, and dried. Recrystallization of the solid from ethanol (1,200 ml) gave title compound as yellow needles, 13.5g (58.5%), m.p. 190°–191°, $\lambda_{max}$. (EtOH) 226, 310 nm., ($\epsilon$ 11,500, 21,000), $\nu_{max}$. (Nujol) 1338 and 1502 (NO$_2$), 972 cm.$^{-1}$ (trans CH=CH), $\tau$ (CF$_3$CO$_2$H) values include 2.15, 2.68 (AB quartet, J 17; trans CH=CH), 7.15 (CH$_3$).

EXAMPLE 66 trans-5-Methyl-3-p-aminostyryl-1,2,4-oxadiazole.

trans-5-Methyl-3-p-nitrostyryl-1,2,4-oxadiazole (6.93g) was dissolved in acetone (400 ml) at about 30°. 15% Acidic titanous chloride solution (250 ml) was added with stirring during 30 min. after which the reaction mixture remained purple in colour The acetone was then removed under reduced pressure and the residual mixture cooled to 5°. The crystalline precipitate was filtered off and washed with cold 2N-hydrochloric acid (15 ml). The solid was dissolved in water (400 ml) and the solution neutralized by the addition of sodium carbonate. The mixture was extracted with chloroform (400 ml). The extract was dried (MgSO$_4$) and the chloroform removed under reduced pressure to give title compound as pale yellow needles, 5.61g (93%), m.p. 139°–140°. $\lambda_{max}$. (EtOH) 231, 335 nm., ($\epsilon$ 10,700, 22,000) $\xi_{max}$. (CHBr$_3$) 3490, 3398 (NH$_2$), 967 cm.$^{-1}$ (trans CH=CH), $\tau$ (CDCl$_3$) values include 2.39 and 3.18 (AB quartet, J = 16; trans CH=CH), 7.42 (CH$_3$).

EXAMPLE 67 trans-5-Methyl-3-p-thiocyanatostyryl-1,2,4-oxadiazole.
A solution of sodium nitrite (0.40g) in water (1.5 ml) was added during 15 min. at 0° to a stirred solution of trans-5-methyl-3-p-aminostyryl-1,2,4-oxadiazole (1.01 g) in glacial acetic acid (30 ml) and 2N-sulphuric acid (10 ml). The solution was maintained at 5° for 1 hr. and then added during 30 min. to a stirred solution of potassium thiocyanate (15g) and cuprous thiocyanate (1.5g) in water (15 ml). The mixture was kept at room temperature for 18 hr. and then poured into saturated sodium hydrogen carbonate solution (200 ml) and extracted with chloroform (200 ml). The extract was dried (MgSO$_4$) and the chloroform removed under reduced pressure. The yellow residue was recrystallized from methanol (8 ml.) and decolourised with charcoal to give title compound, 0.28g (23.2%), m.p. 127°–128°, $\lambda_{max}$ (EtOH) 222, 290 nm., ($\epsilon$ 13,800, 30,700), $\nu_{max}$. (CHBr$_3$), 2170 (SCN), 970 cm.$^{-1}$ (trans CH=CH), $\tau$ (CDCl$_3$) values include 2.60 and 2.95 (AB quartet, J = 16; trans CH=CH) and 7.40 (CH$_3$).

EXAMPLE 68 trans-5-Methyl-3-p-cyanostyryl-1,2,4-oxadiazole.

A solution of sodium nitrite (0.80g) in water (3 ml) was added during 20 min. to a stirred suspension of trans-5-methyl-3-p-aminostyryl-1,2,4-oxadiazole (2.01g) in 2N-sulphuric acid (20 ml) at 5°. The solution was maintained at 10° for one hour and then added during 30 min. to a solution of cuprous cyanide (1.01g) and potassium cyanide (2.28g) in water (8 ml) at 35°. The mixture was then heated to 70° when nitrogen ceased to be evolved. The cooled reaction mixture was filtered and the solid was washed with water and dried. The solid was triturated with boiling chloroform (150 ml) and the chloroform solution was evaporated under reduced pressure to give an orange solid which was recrystallised from ethanol (15 ml) with charcoal decolourisation to give title compound 0.62g (29.5%), m.p. 162°–163°, $\lambda_{max}$. (EtOH) 288 nm, $\epsilon$ 32,300, $\nu_{max}$ (CHBr$_3$) 2250, (CN) 972 cm.$^{-1}$ (trans CH=CH), $\tau$ (CDCl$_3$) values include 2.27 and 2.87 (AB quartet, J = 16; trans CH=CH) and 7.36 (CH$_3$).

EXAMPLE 69

5-Chloromethyl-3-trans-p-methylthiostyryl-1,2,4-oxadiazole.

Chloroacetyl chloride (8.5 ml., 12.1g) was added dropwise to a stirred suspension of p-methylthiocinnamamidoxime (10.4g) in chloroform (100 ml) and dry pyridine (8.5 ml) at 0°. The resulting clear orange solution was stirred at room temperature for 3 hr. and was allowed to stand overnight. Removal of the solvent gave a sticky yellow solid which was dissolved in chloroform (200 ml), and the solution was washed successively with water (50 ml), saturated aqueous sodium bicarbonate (50 ml), aqueous 2N hydrochloric acid (50 ml), and water (2 × 50 ml), and was dried (MgSO$_4$). The solvent was removed, and the residue crystallised from methanol to give the title oxadiazole (9.58g, 72%) as yellow needles, m.p. 95°–96.5° $\lambda_{max}$. (EtOH) 236, 324 nm, ($\epsilon$ 12,500, 29,900)$\nu_{max}$. (CHBr$_3$) 968 cm.$^{-1}$ (trans-CH=CH), $\tau$ (CDCl$_3$) 2.32 and 3.04 (AB-quartet, J 16; trans-CH=CH), 2.52 and 2.77 (aromatic), 5.32 (CH$_2$), 7.52 (SCH$_3$).

EXAMPLE 70

5-Chloromethyl-3-trans-p-methylsulphinylstyryl-1,2,4-oxadiazole.

Peracetic acid (40%, 1.9 ml) was shaken with methylene chloride (20 ml) and the lower layer was separated, and added dropwise at 0° to a stirred solution of 5-chloromethyl-3-trans-p-methylthiostyryl-1,2,4-oxadiazole (2.668g) in methylene chloride (30 ml). The solution was evaporated to dryness after 3 days, and the residue was recrystallised from ethanol to give the sulphoxide as colourless needles (2.348g, 83%), m.p. 156°–158°, $\lambda_{max}$. (EtCH) 221, 282, 288, 304 (infl.) nm, ($\epsilon$ 13,400, 30,250, 32,500, 19,900) $\nu_{max}$. (Nujol) 978 (trans-CH=CH), 1047 (S-O) cm.$^{-1}$, $\tau$ (Me$_2$SO-d$_6$) values include 2.14 and 2.55 (AB quartet, J 16, trans- CH=CH). The mother-liquors yielded a second crop (230 mg, 8%), m.p. 158°–159°.

EXAMPLE 71

3-trans-p-Methylthiostyryl-5-propyl-1,2,4-oxadiazole

A mixture of p-methylthiocinnamamidoxime (10.0g., 48 mM) and butyric anhydride (50 ml., 49.8 g., 314 mM) was heated on a steam-bath for 45 min. and was then cooled and poured into water (400 ml.). The mixture was neutralised by the addition of sodium bicarbonate and was then extracted with ether (2 × 300 ml.). The combined extracts were washed with saturated aqueous sodium bicarbonate (3 × 250 ml.) and with water (200 ml.) and were dried ($Na_2SO_4$). Removal of the solvent gave a yellow oil which crystallised with difficulty. The crude product was triturated with petroleum (b.p. 60°–80°) (15 ml.) and was filtered to give the oxadiazole (4.70g., 38%) as yellow needles, m.p. 34°–35°. $\lambda_{max}$. (EtOH) 235, 320 nm., $\epsilon$ 11,500, 24,860.

EXAMPLE 72

3-trans-p-Methylsulphinylstyryl-5-propyl-1,2,4-oxadiazole.

In a similar manner to that described in Example 64 3-trans-p-methylthiostyryl-5-propyl-1,2,4-oxadiazole was oxidised to the sulphoxide (85%), m.p. 123.5°–124.5°, $\lambda_{max}$. (EtOH) 288 nm., $\epsilon$ 33,000.

EXAMPLE 73

3-trans-p-Methylsulphonylstyryl-5-propyl-1,2,4,-oxadiazole

In a similar manner to that described in Example 43 3-trans-p-methylthiostyryl-5-propyl-1,2,4-oxadiazole was converted into the sulphone (81%), m.p. 125.5°–126.5°, $\lambda_{max}$. (EtOH) 277 (inflex) 285 nm., $\epsilon$ 32,720 and 34,370.

EXAMPLE 74

5-Isopropyl-3-trans-p-methylthiostyryl-1,2,4-oxadiazole

In a similar manner to that described in Example 71 p-methylthiocinnamamidoxime and isobutyric anhydride gave the title oxadiazole (52%), m.p. 38°–40°, $\lambda_{max}$. (EtOH) 235, 319 nm., $\epsilon$ 11,320 and 23,600.

EXAMPLE 75

5-Isopropyl-3-trans-p-methylsulphinylstyryl-1,2,4-oxadiazole

In a similar manner to that described in Example 64 5-isopropyl-3-trans-p-methylthiostyryl-1,2,4-oxadiazole was oxidised to the title sulphoxide (74%), m.p. 74.5°–76°, $\lambda_{max}$. (EtOH) 288 nm., $\epsilon$ 29,660.

EXAMPLE 76

5-Isopropyl-3-trans-p-methylsulphonylstyryl-1,2,4-oxadiazole.

In a similar manner to that described in Example 43 5-isopropyl-3-trans-p-methylthiostyryl-1,2,4-oxadiazole was oxidised to the sulphone (80%), m.p. 102°–103°, $\lambda_{max}$. (EtOH) 277 (inflex), 285 nm. $\epsilon$ 32,840 and 34,230.

EXAMPLE 77

Tablets

| | |
|---|---|
| 3-trans-p-Methylsulphinylstyryl-5-methyl-1,2,4-oxadiazole | 250 mg. |
| Polyethylene Glycol 6000 | 7.5 mg. |
| Magnesium Stearate | 2.5 mg. |

The active ingredient is ground to a powder having a particle size between 1 and 10 microns. It is then granulated with the aid of a chloroform solution of the polyethylene glycol by passing it through a No. 12 mesh British standard sieve, and dried in vacuo. The dried granulate is passed through a No. 16 mesh British standard sieve. The granulate is then blended with the magnesium stearate which acts as a lubricant and compressed on 8 mm punches, preferably having a breakline. Each tablet weighs 260 mg. These tablets may if desired be film-coated in conventional manner.

EXAMPLE 78

Capsules

| | |
|---|---|
| 3-trans-p-Methylsulphinylstyryl-5-methyl-1,2,4-oxadiazole | 250 mg. |
| Highly dispersed silica | 5 mg. |

The finely ground active ingredient and silica are blended and passed through a 100 mesh British standard sieve. The mixture is homogenised prior to filling into hard gelatine capsules. Each capsule contains 255 mg. of the mixture.

The following Preparations illustrate the preparation of unknown compounds used as starting materials for intermediates used in the foregoing Examples.

Preparations 1–9 were carried out in a manner similar to that described in Example 2a.

Preparation 1 m-Chlorocinnamamidoxime

Yield 38.5%. The free amidoxime could not be crystallised. The hydrochloride, obtained in 24% yield, had m.p. 195°–197°, $\lambda_{max}$. (EtOH) 277 nm, $\epsilon$ 20850.

Preparation 2 o-Chlorocinnamamidoxime

Yield 55%, m.p. 113°–115°, $\lambda_{max}$. (EtOH) 270 nm. $\epsilon$ 14730.

Preparation 3 p-Fluorocinnamamidoxime

Yield 75%, m.p. 118°–120°, $\lambda_{max}$. (EtOH) 269 nm., $\epsilon$ 18440.

Preparation 4 p-Bromocinnamamidoxime

Yield 58%, m.p. 130°–131° (aqueous methanol), $\lambda_{max}$. (EtOH) 277 nm. $\epsilon$ 20400.

Preparations 5 p-Trifluoromethylcinnamamidoxime

Yield 69%, m.p. 133°, $\lambda_{max}$. (EtOH) 263, 300nm, $\epsilon$ 16000, 14000

Preparation 6 p-Methylcinnamamidoxime

Yield 53%, m.p. 136°–139°, $\lambda_{max}$. (EtOH) 282 nm. $\epsilon$ 17970.

Preparation 7 p-Methoxycinnamamidoxime

Yield 48.5%, m.p. 165°–167°, $\lambda_{max}$. (EtOH) 290 nm. $\epsilon$ 26100.

Preparation 8 p-Chloro-α-methylcinnamamidoxime

Yield 75%, m.p. 130°–131°, $\lambda_{max}$. (EtOH) 266 nm. $\epsilon$ 18270.

Preparation 9 p-Methylthiocinnamamidoxime

Yield 57%, m.p. 135°–141°, $\lambda_{max}$. 230, 311 nm. $\epsilon$ 12700, 27500.

Preparation 10 m-Chlorocinnamonitrile m-Chlorocinnamamide (1.39 g.) was mixed with sodium metabisulphite (0.72 g.) and phosphoryl chloride (3 ml.). The mixture was heated on the steam-bath for 2.5 hr. and the phosphoryl chloride removed under reduced pressure. The residue was washed well with water, leaving slightly impure m-chlorocinnamonitrile (0.744 g., 59.5%). Recrystallisation from aqueous acetone gave m-chlorocinnamonitrile, m.p. 56°–57°, $\lambda_{max}$. (EtOH) 226, 270 nm. $\epsilon$ 19000, 22500.

Preparation 11 p-Fluorocinnamonitrile p-Fluorocinnamaldehyde (9.0 g.) was refluxed for 1 hr. in 98% formic acid containing sodium formate (10 g.) and hydroxylamine hydrochloride (7 g.). The solution was cooled and poured into water (275 ml.), giving a solid. This was washed well with water, leaving p-fluorocinnamonitrile (6.21 g., 70%), m.p. 64°–65°, $\lambda_{max}$. (EtOH) 271 nm $\epsilon$ 22500.

Preparation 12 p-Chloro-α-methylcinnamonitrile

Following the method of Preparation 11 this compound was prepared in 88% yield, m.p. 54°–58°, $\lambda_{max}$. (EtOH) 270 nm, $\epsilon$ 22600.

Preparation 13

2-Chloro-3-p-methylthiophenylpropionitrile p-Aminothioanisole (10 g.) was added to concentrated hydrochloric acid (20.5 ml.) and water (12 ml.). The mixture was stirred at 0°–5° and sodium nitrite (5.04 g.) in water (29 ml.) added during 1 hr. After being kept at 0° for 1.5 hr. the solution was filtered, and the filtrate added to acrylonitrile (3.82 g.), acetone (5 ml.), and sodium acetate (24 g.). The mixture was stirred at 5°–10° and cupric chloride dihydrate (3 g.) in water (6 ml.) was added during 2 hr. Stirring was continued overnight, then the solvent was removed under reduced pressure, and the residual dark oil extracted with chloroform. The chloroform solution was washed with sodium hydrogen carbonate and with water, dried ($Na_2SO_4$), and evaporated. The residue was distilled under reduced pressure, giving 2-chloro-3-p-methylthiophenylpropionitrile (3.1 g., 20%), b.p. 140°–165°/1 mm., m.p. 58°–60°, $\lambda_{max}$. (EtOH) 260, 327 nm $\epsilon$ 15300, 9970.

Preparation 14

2-Chloro-3-p-Trifluoromethylphenylpropionitrile

Following the method of Preparation 13 this compound was prepared in 57% yield; it had b.p. 103°–106°/1 mm, $\lambda_{max}$. (EtOH) 263 nm $\epsilon$ 650.

Preparation 15 p-Methylthiocinnamonitrile

2-Chloro-3-p-methylthiophenylpropionitrile (2.978 g.) and dry triethylamine (6 ml.) were refluxed for 1.25 hr. The mixture was cooled and poured into 2N hydrochloric acid (20 ml.) with stirring, and the solid filtered off, washed with water, and dried to give the nitrile (2.075 g., 86%), m.p. 58°–65°. Recrystallisation from aqueous methanol gave p-methylthiocinnamonitrile, m.p. 79°, $\lambda_{max}$. (EtOH) 237, 330 nm., $\epsilon$ 11800, 28500.

Preparation 16 p-Trifluoromethylcinnamonitrile

Following the method of Preparation 15 this compound was prepared in 80% yield; it had m.p. 97.5°–98.5°, $\lambda_{max}$. (EtOH) 266 nm., $\epsilon$ 25600.

Preparation 17 p-Chloro-α-methylcinnamaldehyde p-Chlorobenzeldehyde (25 g.) was dissolved in dry ethanol (100 ml.), propionaldehyde (10 ml.) added, and the mixture cooled to 10°. A solution of potassium hydroxide (2 g.) in water (2 ml.) was added to this mixture dropwise with stirring. The reaction mixture was then stirred at room temperature for 3 hrs. More propionaldehyde (5 ml.) was added and the mixture stirred for a further hour. The orange-brown solution was neutralised to pH 7 with 2N hydrochloric acid solution, filtered, and evaporated to dryness in vacuo. The residue was distilled under high vacuum to yield p-chloro-α-methylcinnamaldehyde (16.5 g., 51%) b.p. 120°–125°/0.8 mm. $\lambda_{max}$. (EtOH) 281 nm., $\epsilon$ 10270.

Preparation 18 p-Fluorocinnamaldehyde

This compound was prepared following the procedure of Preparation 17 starting from p-fluorobenzaldehyde and acetaldehyde. Yield, 47%. b.p. 80°–95°/2 mm., $\lambda_{max}$. (EtOH) 220, 285 nm., $\epsilon$ 10500, 23400.

Preparation 19 m-Chlorocinnamamide m-Chlorocinnamic acid (5 g.) was heated with phosphorus pentachloride (10 g.) and phosphoryl chloride (13 ml.) for 2 hr. on the steam-bath. The phosphoryl chloride was then removed under reduced pressure, and the residue in benzene (100 ml.) added with stirring to ammonia solution (d 0.88, 150 ml.) at 15°, giving the crude amide (3.1 g., 62%). Recrystallisation from aqueous acetone gave m-chlorocinnamamide, m.p. 180°, $\lambda_{max}$. (EtOH) 268 nm, $\epsilon$ 19850.

Preparation 20

3-(5-Chlorothien-2-yl)acrylonitrile.

A solution of 2-chloro-5-formylthiophene (5.68 g., 40 mM) and cyanomethylenetriphenylphosphorane (12.04 g., 40 mM) in chloroform (100 ml.) was heated under reflux for 20 min., and was evaporated to an oily solid. This was triturated with ether (20 ml.) and colourless needles of triphenylphosphine oxide (m.p. 156°–157°) were filtered off, and were washed with ether (10 ml.). The combined filtrates were evaporated, and the residue was distilled under reduced pressure to give 3-(5-chlorothien-2-yl)acrylonitrile (5.62 g., 83%) as a colourless oil, b.p. 100°–104°/0.6mm., which crystallised in needles, m.p. 41°–43° [Found: C, 49.1; H, 2.5; Cl, 21.1; N, 8.3; S, 19.1; $C_7H_4ClNS$ (169.6) requires C, 49.6; H, 2.4; Cl, 20.9; N, 8.3; S, 18.9%]$\lambda_{max}$. 315 nm ($\epsilon$ 21,120).

Preparation 21

-(5-Chlorothienyl-2yl)acrylamidoxime 3-(5-Chlorothien-2-yl)acrylonitrile (1.70g., 10mM) was added to a solution of hydroxylamine hydrochloride (1.40g., 20mM) and sodium carbonate (2.12g., 20mM) in water 20 ml.), and sufficient ethanol was added for homogeneity. The solution was refluxed for 30 min., cooled, and was poured into water (250ml.). The crystalline precipitate was filtered off, and was washed with water and dried. Recrystallisation from benzene gave the 3-(5-chlorothienyl-2-yl)acrylamidoxime (0.89g., 46%) as pale yellow needles, m.p. 115° [Found: C, 41.6; H, 3.4; Cl, 17.3; N, 13.9; S, 15.9. $C_7H_7Cl N_2OS$ (202.7) requires C, 41.3; H, 3.5; Cl, 17.4; N, 13.8; S, 15.8%] $\lambda_{max}$. 251 and 316 nm ($\epsilon$6000 and 21,000).

Preparation 22

2Chloro-3-p-methylsulphinylphenylpropionitrile.

Sodium nitrite (42.6g) in water (127 ml.) was added over 20 min. with stirring at 4°–5° to p-methylsulphinylaniline (S. Ghertsetti and M. Pellotti, Gazzetta, 1963, 93. 1000) (94.5 g., 0.61 mole) in water (127 ml.), to which concentrated hydrochloric acid (202 ml.) had been added. After 30 min. more, the solution was added to acetone (40.5 ml.) and acrylonitrile (40.5 ml.) at 4°–5° and the pH brought to ca. 4 with sodium acetate. Cupric chloride dihydrate (31.2g.) in water (35 ml.) was added to the stirred mixture below 5° and stirring continued for 16 hr. The product was extracted with chloroform (2 × 1 l.) and the organic layer washed with saturated NaHCO$_3$ solution (1 l.), and water (1.5 l.). The solution was dried and evaporated to give the crude product (131.6 g., 95%). A sample chromatographed on silica gel and eluted with ethyl acetate. The product crystallized partly over 3 weeks, so benzene was added and the needles separated giving the nitrile, m.p. 88°–90°, $\lambda_{max}$. 227 nm, ($\epsilon$ 11,200) [Found: C, 52.8; H, 4.5; N, 5.7. C$_{10}$H$_{10}$ClNOS requires C, 52.7; H, 4.4; N, 6.1%].

Preparation 23 trans-p-Methylsulphinylcinnamonitrile.

Triethylamine (176 ml.) and dry methanol (35ml.), containing 2-chloro-3-p-methylsulphinyl-phenylpropionitrile (131.0 g., 0.578 mole), were refluxed for 2 hr. cooled and the cold solution was poured into 2-N-hydrochloric acid (865 ml.). The product was extracted with ethyl acetate (1 hr + 2×500 ml.), the extracts being washed with saturated NaHCO$_3$ solution (865 ml.) and a saturated sodium chloride solution (1 l.). The dried extracts were evaporated and the solid residue was treated with ethyl acetate (35 ml.). The solution was filtered to give the nitrile (54.5 g., 49%) m.p. 115-117°, $\lambda_{max}$. 282 nm ($\epsilon$ 22700) [Found: C, 62.2; H, 5.1; N, 6.9. C$_{10}$H$_9$NOS requires C, 62.8; H,4.75; N,7.3%].

Preparation 24 trans-p-Methylsulphinylcinnamamidoxime.

Methanol (ca. 80ml.), containing p-methylsulphinyl-cinnamonitrile (6.685 g., 35 mmole) and hydroxylamine [from hydroxylamine hydrochloride (3.64 g.,)], was refluxed for 4 hr. and kept 16 hr. at 20°. Evaporation of the solution was followed by distribution of the residue between ethyl acetate (250 ml.) and 2N-hydrochloric acid (280 ml.). The acid layer were brought to pH 6–7 with solid NaHCO$_3$ and the solution extracted with ethyl acetate (3 × 250 ml.). The dried or anic layers were combined and evaporated to dryness. A second distribution between ethyl acetate (20 ml.) and 2N-hydrochloric acid (40 ml.) was followed by basification of the aqueous layer to pH 7 and extraction into ethyl acetate (3 × 100 ml.). These extracts were washed with saturated sodium chloride solution and dried. Evaporation left the amidoxime (2.28 g., 29%), m.p. 169–173°. Continuous extraction of the aqueous layer with ethyl acetate for 16 hr. gave more amidoxime (2.48 g., 31%), m.p. 155-160°. An analytical specimen had $\lambda_{max}$. 299 nm, ($\epsilon$ 16,800) [Found: C, 53.7; H, 5.7; N, 11.7. C$_{10}$H$_{12}$N$_2$O$_2$S requires C, 53.6; H, 5.4; N, 12.5%].

Preparation 25 o-Nitrocinnamamidoxime

A solution of hydroxylamine prepared from hydroxylamine hydrochloride (8.34 g.) in methanol (150 ml.) by neutralisation with sodium methoxide was added to o-nitrocinnamonitrile (6.96 g.) (S. Malinowski, Roczniki Chem., 1952, 26, 85) and the mixture was refluxed for 2 hr., then evaporated to ca. 15 ml. under reduced pressure. Ethyl acetate (150 ml.) was added, and the solution was extracted with 2N-hydrochloric acid (2 × 150 ml.). The acid extracts were neutralised with solid sodium hydrogen carbonate, giving a solid (3.3 g., 40%). Recrystallisation from aqueous methanol gave o-nitrocinnamamidoxime, m.p. 173°, $\lambda_{max}$. 236, 265 nm, ($\epsilon$ 17150, 14700) (Found: C, 52.4; H, 4.5; N, 20.05. C$_9$H$_9$N$_3$O$_3$ requires C, 52.2; H, 4.4; N, 20.3%).

Preparation 26 m-Nitrocinnamamidoxime

Prepared similarly to the method of Preparation 25 M.p. 180°–181° (from aqueous methanol), $\lambda_{max}$. (EtOH) 257 nm, $\epsilon$ 20900 (Found: C, 51.8; H, 4.0; N, 19.8. C$_9$H$_9$N$_3$O$_3$ requires C, 52.2; H, 4.4; N, 20.3%).

Preparation 27

3-(5-Methylthiothiene-2-yl)acrylonitrile.

A solution of 2-formyl-5-methylthiothiphene (9.11 g., 58 mmole) and cyanomethylenetriphenylphosphorane (19.1 g., 64 mmole) in chloroform (200 ml.) was stirred at room temperature for 1 hr., and was then heated under reflux for 10 mins. to complete the reaction. The solvent was removed, and the residue was triturated with dry ether (50 ml.). Colourless crystals of triphenylphosphine oxide (m.p. 156°–157°), were filtered off, and were washed with ether (10 ml.). The combined filtrates were evaporated, and the dark red oily residue was distilled under reduced pressure to give 3-(5-methylthiothien-2-yl)-acrylonitrile (8.33 g., 80%) as a pale-yellow oil, b.p. 124°–135°/0.7 mm., $\lambda_{max}$. 350, 241 nm, ($\epsilon$ 3440, 1460) [Found (on a redistilled sample): C, 52.9; H, 3.8; N, 7.4; S, 35.7. C$_8$H$_7$NS$_2$ (181.3) requires C, 53.0; H, 3.9; N, 7.7; S, 35.4%].

Preparation 28

3-(5-Methylthiothien-2-yl)acrylamidoxime.

3-(5-Methylthiothien-2-yl)acrylonitrile (7.0 g., 38.7 mmole) was added to a solution of hydroxylamine hydrochloride (7.70 g., 77.4 mmole) and sodium carbonate (8.20 g., 77.6 mmole) in water, and ethanol was added to give a homogeneous solution. This was heated under reflux for 5 hr., and the ethanol was then removed under reduced pressure. The Mixture was extracted with ethyl acetate, and the combined organic solutions were extracted with 2N-hydrochloric acid. The acid solution was then neutralised with sodium hydrogen carbonate, and the mixture was extracted into ethyl acetate. The organic solution was dried and evaporated to give the crude product as a gum (7.2 g., 87%). A sample purified by chromatography and crystallised from ethanolpetrol had m.p. 70°–71° [Found: C, 43.5; H, 4.5; N, 12.6; S, 28.3. C$_8$H$_{10}$N$_2$OS$_2$ (214.3) requires C, 44.8; H, 4.7; N, 13.1; S, 29.9%]. $\lambda_{max}$. 243, 335 nm ($\epsilon$ 7700, 21400), $\nu_{max}$.(CHBr$_3$) 3600, 3530, 3420, 942 cm.$^{-1}$.

We claim:

1. A compound of the formula

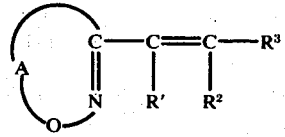

in which A is selected from the group consisting of residues of formula

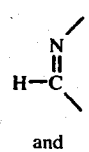

and

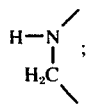

R' and R² are each selected from the group consisting of a hydrogen atom, a halogen atom and a methyl or ethyl group; and R³ is selected from the group consisting of azidophenyl, $C_{1-5}$ alkylthio-phenyl, $C_{1-5}$ alkylsulphinyl-phenyl, $C_{1-5}$ alkylsulphonylphenyl, thiocynatphenyl and alkylthiothienyl.

2. A compound as defined in claim 1 in which said compound is 3-p-methylthiostyryl-1,2,4-oxadiazole.

3. A compound as defined in claim 1 in which said compound is 3-(5-methylthiothien-2-yl)vinyl-1,2,4-oxadiazole.

4. A compound as defined in claim 1 in which the said group R³ is selected from the group consisting of azidophenyl, $C_{1-5}$ alkylthio-phenyl, and $C_{1-5}$ alkylsulphinylphenyl.

5. 3(p-methylsulphinylstyryl)-1,2,4-oxadiazole.

6. 3-(5-chlorothien-2-yl)vinyl-1,2,4-oxadiazole.

7. 3-p-methylsulphinylstyryl-5-methyl-1,2,4-oxadiazole.

8. 3-p-methylsulphinylstyryl-5-ethyl-1,2,4-oxadiazole.

9. 5-amino-3-p-methylsulphinylstyryl-1,2,4, oxadiazole.

* * * * *